United States Patent [19]
Jones et al.

[11] Patent Number: 5,235,006
[45] Date of Patent: Aug. 10, 1993

[54] MESOGENS AND POLYMERS WITH MESOGENS

[75] Inventors: Frank N. Jones, Fargo, N. Dak.; Steven L. Kangas, Woodbury, Minn.; Der-Shyang Chen, Winnipeg, Canada; Adel F. Dimian, Oakdale, Minn.; Daozhang Wang, Fargo, N. Dak.

[73] Assignee: North Dakota State University, Fargo, N. Dak.

[21] Appl. No.: 585,047

[22] Filed: Sep. 18, 1990

Related U.S. Application Data

[63] Continuation of Ser. No. 249,965, Sep. 27, 1988, abandoned, which is a continuation-in-part of Ser. No. 170,907, Mar. 21, 1988, Pat. No. 5,043,192, which is a continuation-in-part of Ser. No. 168,231, Mar. 15, 1988, abandoned, which is a continuation-in-part of Ser. No. 86,504, Aug. 14, 1987, abandoned, which is a continuation-in-part of Ser. No. 31,397, Mar. 27, 1987, abandoned, which is a continuation-in-part of Ser. No. 31,395, Mar. 27, 1987, abandoned.

[51] Int. Cl.$^5$ .................................................. C08G 8/28
[52] U.S. Cl. ...................................... 525/510; 525/528; 528/96; 528/97; 528/98; 528/99; 528/100; 528/101; 428/1
[58] Field of Search ................... 528/99, 100, 101, 87, 528/96, 97, 98; 525/510, 528

[56] References Cited

U.S. PATENT DOCUMENTS

| | | | |
|---|---|---|---|
| 2,465,319 | 3/1949 | Whinfield et al. | 260/75 |
| 2,589,688 | 3/1952 | Florey et al. | 260/75 |
| 2,600,376 | 6/1952 | Caldwell | 260/47 |
| 2,755,273 | 7/1956 | Bock | 260/47 |
| 3,052,653 | 9/1962 | Iannicelli | 260/75 |
| 3,185,668 | 5/1965 | Meyer et al. | 260/75 |
| 3,418,276 | 12/1968 | Izard | 260/47 |
| 3,476,697 | 11/1969 | Clements et al. | 260/22 |
| 3,551,380 | 12/1970 | Kohayashi et al. | 260/45.7 |
| 3,646,108 | 2/1972 | Jones et al. | 260/473 G |
| 3,650,999 | 3/1972 | Martins et al. | 260/22 D |
| 3,652,502 | 3/1972 | Jackson, Jr. et al. | 260/75 R |
| 3,674,724 | 7/1972 | Marzocchi | 260/3 |
| 3,707,516 | 4/1971 | Walus | 260/21 |
| 3,772,064 | 11/1973 | Mendelsohn et al. | 117/122 P |
| 3,787,370 | 1/1974 | Shima et al. | 260/75 R |
| 3,804,805 | 4/1974 | Kuhfuss et al. | 260/47 C |
| 3,836,491 | 9/1974 | Taft et al. | 260/22 TN |
| 3,926,920 | 12/1975 | Georgoudis et al. | 260/75 R |
| 3,932,326 | 1/1976 | Hoh et al. | 260/26 |
| 3,954,900 | 5/1976 | Schmalz et al. | 260/850 |
| 3,991,034 | 11/1976 | Takeo et al. | 260/75 NK |
| 3,994,851 | 11/1976 | Chang | 260/29.4 R |
| 4,010,126 | 4/1975 | Kuzma | 260/225 B |
| 4,012,363 | 3/1977 | Brüning et al. | 260/75 R |
| 4,045,399 | 8/1977 | Suzuki et al. | 260/29.6 N |
| 4,060,516 | 11/1977 | Kuratsuji et al. | 260/75 T |
| 4,072,662 | 2/1978 | van der Linde et al. | 260/75 R |
| 4,075,173 | 2/1978 | Maruyama et al. | 260/47 C |
| 4,130,549 | 12/1978 | Ueno et al. | 528/93 |
| 4,223,125 | 9/1980 | Bier et al. | 528/305 |
| 4,261,873 | 4/1981 | Laganis et al. | 260/29.2 E |
| 4,267,239 | 5/1981 | Thankachan et al. | 428/425.1 |
| 4,267,304 | 5/1981 | Feasey et al. | 528/193 |
| 4,271,062 | 6/1981 | Boomgaard et al. | 260/39 P |
| 4,293,435 | 10/1981 | Portugall et al. | 252/299.01 |
| 4,315,086 | 2/1982 | Ueno et al. | 525/391 |
| 4,331,782 | 5/1982 | Linden | 525/173 |
| 4,335,188 | 6/1982 | Igi et al. | 428/458 |

(List continued on next page.)

FOREIGN PATENT DOCUMENTS 0007574 7/1979 European Pat. Off. .
0226847 11/1986 European Pat. Off. .
0138768 8/1987 European Pat. Off. .

(List continued on next page.)

OTHER PUBLICATIONS

Chem. Abstracts 114:186201s Articulated rigid-rod polymers containing benzobisoxazole and benzobisthiazole moieties.

(List continued on next page.)

*Primary Examiner*—Ralph H. Dean, Jr.
*Attorney, Agent, or Firm*—Fitch, Even, Tabin & Flannery

[57] ABSTRACT

Novel mesogens, epoxy resins and the synthesis thereof as well as coating binders for coating compositions based upon the mesogens and epoxy resins are described.

12 Claims, 1 Drawing Sheet

U.S. PATENT DOCUMENTS

| | | | |
|---|---|---|---|
| 4,338,412 | 7/1982 | von Bonin | 521/157 |
| 4,398,022 | 8/1983 | Sublett | 528/302 |
| 4,401,805 | 8/1983 | Weemes et al. | 528/302 |
| 4,413,015 | 11/1983 | Anderson et al. | 426/131 |
| 4,419,507 | 12/1983 | Sublett | 528/302 |
| 4,435,546 | 3/1984 | Bier et al. | 525/418 |
| 4,436,896 | 3/1984 | Okamoto et al. | 156/332 |
| 4,439,586 | 3/1984 | Kawakami et al. | 525/169 |
| 4,446,302 | 5/1984 | Sandhu et al. | 528/302 |
| 4,465,815 | 8/1984 | Chattha | 525/443 |
| 4,522,971 | 6/1985 | DeBergalis | 524/547 |
| 4,552,814 | 11/1985 | Cavitt et al. | 428/414 |
| 4,554,343 | 11/1985 | Jackson, Jr. et al. | 528/274 |
| 4,560,741 | 12/1985 | Davis et al. | 528/302 |
| 4,585,854 | 4/1986 | Tung et al. | 528/295 |
| 4,600,768 | 7/1986 | Jackson, Jr. et al. | 528/308 |
| 4,609,691 | 9/1986 | Geist et al. | 523/415 |
| 4,617,371 | 10/1986 | Blumstein et al. | 528/194 |
| 4,631,328 | 12/1986 | Ringsdorf et al. | 526/259 |
| 4,637,896 | 1/1987 | Shannon | 252/299.7 |
| 4,643,937 | 2/1987 | Dickinson et al. | 428/215 |
| 4,652,591 | 3/1987 | Londrigan | 521/172 |
| 4,659,763 | 4/1987 | Gallucci et al. | 524/358 |
| 4,665,150 | 5/1987 | Tesch et al. | 528/98 |
| 4,681,915 | 7/1987 | Bates et al. | 525/148 |
| 4,694,061 | 9/1987 | Pfeifer | 528/125 |
| 4,698,397 | 10/1987 | Toya et al. | 525/437 |
| 4,701,477 | 10/1987 | Altenberg et al. | 521/167 |
| 4,707,990 | 9/1987 | Noonan et al. | 526/304 |
| 4,713,196 | 12/1987 | Praefcke et al. | 252/299.01 |
| 4,725,664 | 2/1988 | Halmess et al. | 528/176 |
| 4,728,718 | 3/1988 | Morris et al. | 528/306 |
| 4,745,135 | 5/1988 | Thomas et al. | 521/114 |
| 4,745,136 | 5/1988 | Thomas et al. | 521/114 |
| 4,745,137 | 5/1988 | Thomas et al. | 521/137 |
| 4,757,830 | 8/1988 | Kageyama et al. | 525/450 |
| 4,758,616 | 7/1988 | Okano et al. | 524/399 |
| 4,762,901 | 8/1988 | Dhein et al. | 528/73 |
| 4,764,581 | 8/1988 | Muller et al. | 528/100 |
| 4,780,524 | 10/1988 | Dobbelstein et al. | 528/104 |
| 4,782,132 | 11/1988 | Nozawa et al. | 528/193 |
| 4,785,074 | 11/1988 | Pfeifer | 528/353 |
| 4,797,465 | 1/1989 | Portugall et al. | 528/176 |
| 4,801,734 | 1/1989 | Koch | 560/73 |
| 4,814,426 | 3/1989 | Utsumi et al. | 528/272 |
| 4,830,722 | 5/1989 | Dobbelstein et al. | 204/181 |
| 4,855,366 | 8/1989 | Cavitt | 525/533 |
| 4,855,484 | 8/1989 | Müller et al. | 560/72 |
| 4,868,230 | 9/1989 | Rao et al. | 523/403 |
| 4,868,250 | 9/1989 | DeMartino et al. | 525/479 |
| 4,877,858 | 10/1989 | Hachiya et al. | 528/100 |
| 4,888,381 | 12/1989 | Pankratz | 524/751 |
| 4,894,263 | 1/1990 | Dubois et al. | 428/1 |
| 4,915,491 | 4/1990 | DeMartino et al. | 350/330 |
| 4,962,163 | 10/1990 | Hefner | 525/463 |

FOREIGN PATENT DOCUMENTS

| | | |
|---|---|---|
| 252357 | 1/1988 | European Pat. Off. . |
| 252358 | 1/1988 | European Pat. Off. . |
| 252359 | 1/1988 | European Pat. Off. . |
| 305795 | 3/1989 | European Pat. Off. . |
| 1904110 | 12/1977 | Fed. Rep. of Germany . |
| 3601560 | 7/1987 | Fed. Rep. of Germany . |
| 3622613 | 1/1988 | Fed. Rep. of Germany . |
| 44-001079 | 1/1969 | Japan . |
| 45-022011 | 8/1970 | Japan . |
| 52-073929 | 7/1971 | Japan . |
| 51-044130 | 4/1976 | Japan . |
| 51-056839 | 5/1976 | Japan . |
| 53-113900 | 10/1978 | Japan . |
| 56-005275 | 2/1981 | Japan . |
| 60-044347 | 10/1985 | Japan . |
| 62-068809 | 3/1987 | Japan . |
| 1-172468 | 7/1989 | Japan . |
| 1115919 | 9/1984 | U.S.S.R. . |
| 1146694 | 3/1969 | United Kingdom . |

OTHER PUBLICATIONS

Che. Abstracts 103: 14247c Thermally anisotropic aromatic polyesters, Agency of Indust'l Sciences and Technology, Jpn. Kokai Tokkyo Koko JP 60,101,117.

Liquid Crystal Polymer II/III, Editor Gordon 1984, Liquid Crystalline Side Chain Polymers and Other Polymers in an Electric Field, Ringsdorf and Zentel.

Makromol Chem. 183, 1245–1256.

*Advances in Polymer Science* 59, 1–158.

*Macromolecules* 1983, 16, 1677–1678 Shannon.

*Macromolecules* 1984, 17, 1873–1876 Shannon.

Crowie et al., "Thermotropic Liquid Crystalline Main--Chain Polyesters Containing Cyclooctyl Units," *Macromolecules* 1988, 21, 2865–2869, filed in Ser. No. 31,397.

*Chemical Abstracts* 85:79835n entitled "Polyester resin powder coating compositions" (Abstract of SHO 51(1976)44130).

*Chemical Abstracts* 85:110, 175y entitled "Blocking—resistent resin powder coating compostions" (Abstract of SHO 51(1976)56839).

*Chemical Abstracts* 88:8624u entitled "Polyester powder coating compositions" (Abstract of SHO 52(1977) 73929).

Blumstein et al., "Oriented Polymer Growth In Mesophases," *Macrmolecules*, 1975, vol. 8, No. 1 Jan.–Feb.

Polymer Letters Edition vol. 14, pp. 757–760 (1976) "Crosslinking of Lyotropic Liquid Crystals In Magnetid Fields."

Tsutsui et al., "Network Polymers With Cholesteric Liquid Crystalline Order Prepared From Poly (-butyl L-glutamate)-butyl acrylate liquid crystalline," *Polymer* vol. 22, Jan. (1981).

Zental et al., "Liquid Crystalline Elastomers Based On Liquid Crystalline Side Group, Main Chain and Combined Polymers," *Makromol. Chem.* 187, 1915–1926 (1986).

Abstract CA101(12):91537y "Fixation of The Structure (List continued on next page.)

OTHER PUBLICATIONS

Of A Liquid Crystalline Monomers Of The Azomethine Series by Means Of Its Polymerization In The Mesophase," Arslanov, V. V.; Nikolaeva, V. 1. (Moscow) Vysolkomol. Soedin., Ser. B, 26(3), 208–10 (1984).

Browstow et al., "Transmission of Mechanical Energy Through Polymeric Liquid Crystals and Their Blends," *Polymeric Engineering & Science* 48(12) pp. 785–795, Jun. (1988).

Browtow, "Polymer Liquid Crystals in Their Blends," Kunststoffe German Plastics, 78 (1988) 5.

Struktur und Eigenschaften segmentierter Polyetherester, 3ª) Synthese of de finierter Oligomerer des Polybutylenterephthalats, Batzer et al., *Makromol. Chem.* 181, 301–232 (1980).

Liquid Crystals, 6 Mesmorphic Phenols and Primary Amines. p-Phenylene Dibenzoates With Terminal Hydroxy and Amine Groups, Schroeder et al., *J. of Org. Chem.* 41, 2566 (1976).

*Water-Soluble Synthetic Polymers:* Properties and Behavior, vol. II by Molyneux, pp. 1 & 2, CRC Press, Inc. Berry, 35(4) Paint Mfrg. 45 (1965)—Chemical Abstract 6(72) 3766y (1965).

Dimian et al., "Model Crosslinkable Liquid Crystal Oligoester Diols as Coatings Binders," *Polymer Mater. Sci. Eng.* 56, 640–644 (Apr. 1987).

Wang et al., "Synthesis of Crosslinkable Liquid-Crystalline Oligoester Diols etc.," *Polym. Mater. Sci. Eng.* 56 645–649 (Apr. 1987).

Graft Copolymers of Para Hydroxybenzoic Acid (PHB). I. General Method for Grafting Mesogenic Oligo-PHB to Oligomers, J. Poly. Sci. Part A: Polymer Chemistry 25, 1109–1125 (Apr. 1987).

Chen et al., "Liquid Crystalline Acrylic Copolymers As Binders For Non-Bake Coatings," *Polym. Mater. Sci. Eng.* 57, 217–221 (1987).

Abstract of Art. entitled "Liquid Crystalline Three Dimensional Crosslinked Networks," Jones et al., the article published in the Proceeding of the First Meeting of the European Polymer Federation at Lyon, France (Sep. 1987).

Binders for Higher-Solids Coatings Part III: Model Alkyd Resins Modified By Liquid Crystalline Groups, Chen et al., J. of Coatings Tech. 60, 39–45 (Jan. 1988), presented at the 65th Annual Meeting of the Federation of Societies For Coatings Technology, Oct. 6, 1987.

Advances in Polymer Science 59, 104–121.

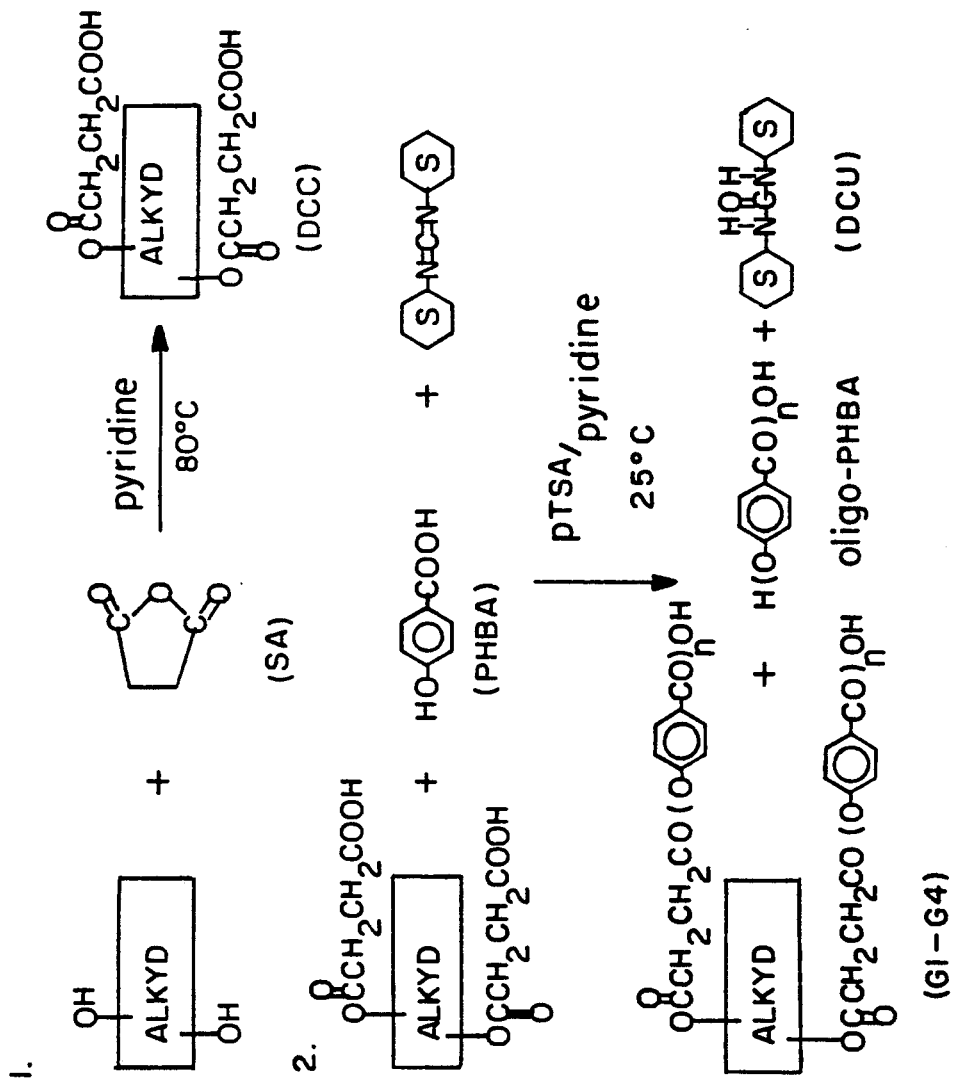
FIG. 1 SYNTHESIS OF PHBA-MODIFIED ALKYDS G1-G4

MESOGENS AND POLYMERS WITH MESOGENS

This application is a continuation of application Ser. No. 249,965 filed Sep. 27, 1988 now abandoned which application is a continuation-in-part application of application Ser. No. 170,907 filed Mar. 21, 1988, now U.S. Pat. No. 5,043,192, which application is a continuation-in-part application of application Ser. No. 168,231 filed Mar. 15, 1988, now abandoned, which application is a continuation-in-part application of application Ser. No. 86,504 filed Aug. 14, 1987, now abandoned, which application is a continuation-in-part application of application Ser. Nos. 031,395 and 031,397, both filed on Mar. 27, 1987 and now abandoned.

BACKGROUND OF INVENTION

Liquid-crystal (L-C) polymers are known to form mesophases having one- and two-dimensional order as disclosed by Flory, P. J., *Advances in Polymer Science, Liquid Crystal Polymers I;* Springer-Verlag: New York (1984) Volume 59; Schwarz, J. Mackromol, Chem. Rapid Commun. (1986) 7, 21. Further, mesophases are well known to impart strength, toughness and thermal stability to plastics and fibers as described by Kwolek et al in *Macromolecules* (1977) 10, 1390; and by Dobb et al, *Advances in Polymer Science, Liquid Crystal Polymers II/III* (1986) 255(4), 179.

While L-C polymers have been widely studied, their potential utility as coatings binders seems to have been overlooked. Japanese patents claiming that p-hydroxybenzoic acid (PHBA), a monomer commonly used in L-C polymers, enhances the properties of polyester powder coatings are among the very few reports that may describe L-C polymers in coatings; Japanese Kokai 75/40,629 (1975) to Maruyama et al; Japanese Kokai 76/56,839 (1976) to Nakamura et al; Japanese Kokai 76/44,130 (1976) to Nogami et al; and Japanese Kokai 77/73,929 (1977) to Nogami et al.

Hardness and impact resistance are two desirable characteristics of coatings. However, because hardness is associated with higher Tgs (glass transition temperatures), and good impact resistance with lower Tgs, there is usually a trade-off between hardness and impact resistance. Further, non-baked polymeric vehicles with low viscosities which provide binder coating films with improved hardness and shorter drying times through combinations of polymers with mesogenic groups are not disclosed in the prior art and are to be desired.

An object of this invention is to provide new and unique mesogenic compositions and a method for making such compositions.

An object of this invention is the provision of modified polymers comprising low Tg polymers covalently bonded with mesogenic groups for use in formulated coatings to provide improved films.

Another object of this invention is to provide a polymeric vehicle which includes a modified polymer which is an epoxy resin covalently bonded to mesogenic groups.

Yet another object of this invention is to provide coatings of improved hardness and impact resistance.

Other important objects are to provide high solids/low viscosity, non-baking formulated coatings comprising polymeric vehicles for providing films wherein the coating formulation is fast drying and provides hard and impact resistant films.

Still further objects and advantages of the invention will be found by reference to the following description.

BRIEF DESCRIPTION OF THE FIGURE

FIG. 1 outlines the synthesis of modified alkyds.

SUMMARY OF THE INVENTION

In accord with this invention a polymeric vehicle is prepared, the polymeric vehicle comprising a modified polymer containing covalently bonded mesogenic groups. This modified polymer may be used as the sole component of a polymeric vehicle for a coating, to which may be added solvents and known additives such as pigments, thereby providing a formulated coating. Optionally the polymeric vehicle comprises a modified polymer in a mixture with other polymers, modified or unmodified, and with cross-linking resins. Solvents and additives may be added to such a mixture of polymers and resins to make a formulated coating. An aspect of the invention is provision of a coating binder which is the polymer portion which includes the modified polymer, of a coating film which has high hardness, flexibility, and impact resistance. After the formulated coating is applied to a base or substrate, solvents (if present) evaporate leaving a solvent-free film. Evaporation may be accelerated by heating, as by baking. In some forms of the invention, no further chemical reaction is necessary to impart useful properties to the resulting solvent-free film. In other forms of the invention, optimum properties are attained only after chemical reactions occur within the film, forming covalent bonds and increasing the molecular weight of the modified polymer and usually converting it into a three-dimensional cross-linked polymeric network. In some cases these chemical reactions occur between the modified polymer and a cross-linking resin if present in the formulated coating. In other cases, the modified polymer may chemically react with substances to which the film is exposed after solvent evaporation, for example, with oxygen in the air. The chemical reactions that form a cross-linked network may be accelerated by heating (baking). It is the provision of this improved film with improved hardness, flexibility and impact resistance, and the coating binder therefor, to which this invention is particularly directed. Since the coating binder primarily provides the desired film characteristics, the properties of the coating binder are particularly described primarily by tests which measure hardness and impact resistance.

This invention also provides for using a polymeric vehicle comprising a modified polymer which after film formation provides a low Tg coating binder which has hardness and impact resistance. We have found that the presence of mesogenic groups covalently bonded to otherwise amorphous polymers provides coating binders that are substantially harder than comparable coating binders not having mesogenic groups and have found that this is obtained without substantially raising Tg of the coating binder. The presence of covalently bound mesogenic groups also imparts other desirable properties to the formulated coating. Thus, according to the invention, it is possible to prepare very hard coating binders and films while retaining the impact resistance, flexibility and adhesion associated with a low Tg. Coating binders with Tgs in a range from $-50$ degrees C. to $+10$ C. are often very elastic and impact resistant, but they are generally too soft to be useful in most coatings applications. On the other hand, non-crosslinked coatings with Tgs above 60 degrees C. are usually hard, but they are generally brittle and have very poor impact resistance. It is, therefore, beneficial to impart hardness to coating binders without sacrificing impact resistance. Moreover, the presence of covalently bound mesogenic groups imparts other desirable properties to the formulated coating. For example, this invention can alleviate a common problem of formulated coatings: that substantial amounts of solvent are required to reduce viscosity to a level low enough for application of polymers whose Tgs and molecular weights are high enough to provide good properties. The use of large amounts of solvent results in increased costs and often in unacceptable levels of atmospheric pollution. Especially large amounts of solvent are often required for conventional coatings vehicles whose Tgs and molecular weight are high enough to impart desirable properties without cross-linking. Presence of mesogenic groups can both improve their properties and reduce the amount of solvent required.

The groups that provide the coating binder of the invention are called "mesogenic groups". The mesogenic groups of this invention are chemical structures that contain a rigid sequence of at least two aromatic rings connected in the para position by a covalent bond or by rigid or semi-rigid chemical linkages. Optionally, one of the rigid aromatic rings may be a naphthalenic rings linked at the 1,5- or 2,6- positions. Modified polymers containing mesogenic groups are called "mesomorphous." The coating binders of this invention contain between 5 percent and 50 percent by weight of mesogenic groups to provide the desired characteristics. When a polymer is referred to as "liquid crystalline" herein it is meant to cover such polymers which exhibit mesophases. The presence of mesophases are often associated with the presence of mesogenic groups.

An important aspect of this invention are the mesogenic compounds

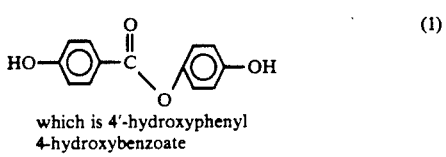

which is 4'-hydroxyphenyl
4-hydroxybenzoate

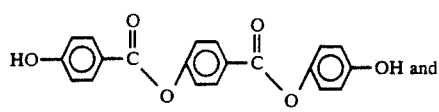

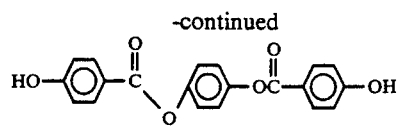

the synthesis thereof and the reaction products of 1, 2 and 3 and mixtures thereof with epoxy polymers such as the diglycidyl ether of Bisphenol A which has the formula

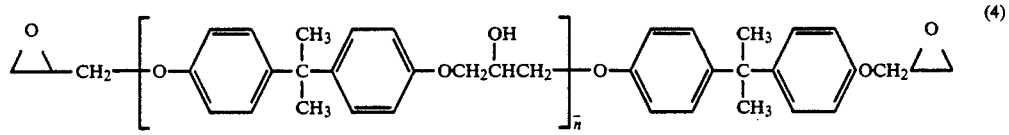

wherein $\bar{n}>0$, preferrably $>0.12$, but not greater than about 20 wherein $\bar{n}$ is an average value.

Yet another important aspect of this invention is the mesogenic epoxy compound having the general formula

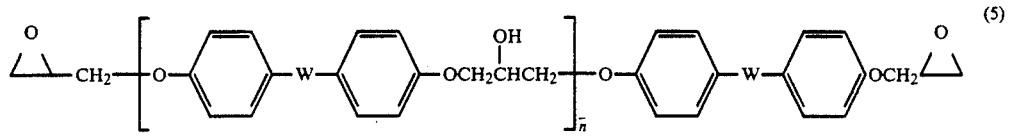

wherein $\bar{n}>0$ but not greater than about 20 wherein n is an average value, W=

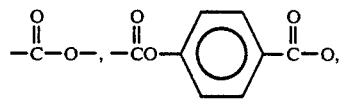

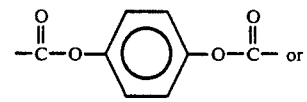

combinations thereof and the synthesis thereof. This epoxy compound is the diglycidyl ether of 4'-hydroxyphenyl 4-hydroxybenzoate (1), formula 2, formula 3 or mixtures thereof. As the term is used herein, this diglycidyl ether (5) of (1), (2) or (3) is an "epoxy polymer" when $\bar{n}>0$.

Epoxies can react with multifunctional epoxy cross-linkers such as di or polyamines through the epoxide groups to give cured films. Epoxies with —OH functionality can also be cured with aminoplast resins such as hexakis (methoxymethyl) melamine resin (HMMM) through the OH groups.

As used in this application, "polymer" means a polymeric or oligomeric component of a coating vehicle such as an epoxy polymer, acrylic polymer or a polyester polymer; alkyd polymers are considered to be a sub-class of polyester polymers. "Cross-linker resin" means a di- or polyfunctional substance containing functional groups that are capable of forming covalent bonds with epoxy hydroxyl, carboxyl and —SH groups that are optionally present on the polymer; aminoplast and polyisocyanate resins are members of this class; melamine resins are a sub-class of aminoplast resins; di or polyamines, carboxylic acids and mercaptans are epoxy resin cross-linkers. "Modified polymer" means a polymer having covalently bound mesogenic groups as described herein and for purposes of this application includes formula (5) wherein n=0. "Polymeric vehicle" means all polymeric and resinous components in the formulated coating, i.e. before film formation, including but not limited to modified polymers. "Coating binder" means the polymeric part of the film of the coating after solvent has evaporated and, in cases where cross-linking occurs, after cross-linking. "Formulated coating" means the polymeric vehicle and solvents, pigments, catalysts and additives which may optionally be added to impart desirable application characteristics to the formulated coating and desirable properties such as opacity and color to the film. "Film" is formed by application of the formulated coating to a base or substrate, evaporation of solvent, if present, and cross-linking, if desired. "Air-dried formulated coating" means a formulated coating that produces a satisfactory film without heating or baking. "Baked formulated coating" means a formulated coating that provides optimum film properties upon heating or baking above ambient temperatures.

Acrylic polymer means a polymer or copolymers of

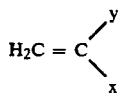

wherein $y = CH_3$ or $H$

R = straight chain or branched alkyls having 1 to 12 carbons,

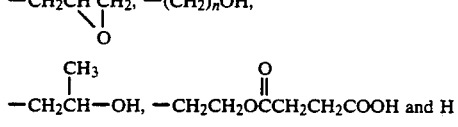

$n = 2$ to 7.

In the case of hydroxy-substituted alkyl acrylates the monomers may include members selected from the group consisting of the following esters of acrylic or methacrylic acid and aliphatic glycols: 2-hydroxy ethyl acrylate; 3-chloro-2-hydroxypropyl acrylate; 2-hydroxy-1-methylethyl acrylate; 2-hydroxypropyl acrylate; 3-hydroxypropyl acrylate; 2,3-dihydroxypropyl acrylate; 2-hydroxybutyl acrylate; 4-hydroxybutyl acrylate; diethylene-glycol acrylate; 5-hydroxypentyl acrylate; 6-hydroxyhexyl acrylate; triethyleneglycol acrylate; 7-hydroxyheptyl acrylate; 2-hydroxy-1-methylethyl methacrylate; 2-hydroxy-propyl methacrylate; 3-hydroxypropyl methacrylate; 2,3-dihydroxypropyl methacrylate; 2-hydroxybutyl methacrylate; 4-hydroxybutyl methacrylate; 3,4-dihydroxybutyl methacrylate; 5-hydroxypentyl methacrylate; 6-hydroxyhexyl methacrylate; 1,3-dimethyl-3-hydroxybutyl methacrylate; 5,6-dihydroxyhexyl methacrylate; and 7-hydroxyheptyl methacrylate.

"Polyester polymers" means the polymerized reaction product of polyacids and polyols; polyacids include diacids such as isophthalic, terephthalic, and fumaric acids and $HOOC(CH_2)_nCOOH$ where $n=2$ to 14 and "dimer acids", anhydrides of diacids such as maleic, phthalic, hexahydrophthalic, and succinic, and anhydrides of polyacids such as trimellitic acid anhydride. The polyols include linear diols such as $HO\,(CH_2)_mOH$ where $m=2$ to 16, branched aliphatic diols such as neopentyl glycol, 1,3-butylene glycol, propylene glycol and 1,3-dihydroxy-2,2,4-trimethylpentane, cycloaliphatic diols such as hydroquinone, 1,4-dihydroxymethylcyclohexane and "hydrogenated Bisphenol A", diol ethers such a diethylene glycol, triethylene glycol and dipropylene glycol, and polyols such as glycerol, pentaerythritol, trimethylol propane, trimethylol ethane, dipentaerythritol, sorbitol and styrene-allyl alcohol copolymer.

Esterification catalysts that are used in the process for preparing polyesters are organo tin catalysts such as butyl stannoic acid (sold under the name Fascat 4100 by M&T Chemicals, Inc.), barium oxide, barium hydroxide, barium naphthenate, calcium oxide, calcium hydroxide, calcium naphthenate, lead oxide, lithium hydroxide, lithium naphthenate, lithium recinoleate, sodium hydroxide, sodium naphthenate, zinc oxide, and lead tallate.

In this invention "alkyd polymers" are considered to be a sub-class of "polyester polymers." Alkyds are condensation polymers of the polyacids and polyols as described above that also contain monobasic acids. The monobasic acids may include saturated or unsaturated fatty acids having between 9 and 26 carbon atoms and monobasic aromatic acids.

Fatty, or other carboxylic, acids that are used to prepare alkyd resins include $HOOC(CH_2)_nCH_3$ where $n=7$ to 22, oleic acid, linolelic acid, linolenic acid, erucic acid, soybean oil fatty acids, linseed oil fatty acids, safflower oil fatty acids, sunflower oil fatty acids, coconut oil fatty acids, tall oil fatty acids, dehydrated castor oil fatty acids, benzoic acid, toluic acid and t-butylbenzoic acid. Fatty acids may be incorporated into the alkyd polymer as such or as a component of triglycerides.

In this application epoxy polymer means a polymer having more than one repeating monomeric unit, the polymer having terminal or pendant epoxy groups

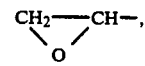

epoxy polymers including a diglycidyl ether of Bisphenol A DGEBPA (see formula 4) the diglycidyl ether of 1, 4 butanediol (DGE-1,-4BD) which is available commercially from Ciba-Geigy, under the name of Araldite RD-2, and the diglycidyl ether of 4'-hydroxyphenyl 4-hydroxybenzoate (see formula 5).

Although it is especially important that covalently bonded mesogenic groups, according to the invention, impart substantially improved hardness to coating binders without sacrificing impact resistance, the mesogenic groups often improve coatings in at least two other ways. In some cases inclusion of modified polymers according to the invention effectively lowers the viscosity of formulated coatings at a given solids content relative to the viscosity of comparable unmodified polymers in comparable solvents at the same solids level. The reason is that mesogenic groups tend to cause modified polymers to form stable dispersions rather than solutions in many common solvents. Thus, less solvent is required, reducing cost and air pollution. Furthermore, in the case of air dried formulated coatings, the mesogenic groups greatly reduce the time necessary for the polymeric vehicle to harden into a film, referred to as "dry-to-touch" time.

We have found that mesogenic groups covalently bound to polymers can improve polymeric vehicles which provide non-epoxy coating binders having a Tg as low as $-50°$ C. or as high as $+60°$ C. while providing improved hardness, adhesion, impact resistance and flexibility. We have found mesogenic groups covalently bound in an epoxy polymer can improve polymeric vehicles which provide coating binders with a Tg as high as $+180°$ C. while providing improved hardness, adhesion, impact resistance and flexibility.

The epoxy polymers of the invention can be used as cured casting resins for any product which can be cast such as in electrical equipment applications, pipes and sport equipment. In such application the epoxy polymers may be cured using polyfunctional amines and commonly known accelerators. Reinforcing fibers such as metal, asbestos, carbon fibers, glass fibers, cotton, polyamide, polyester, polyacrylonitrile or polycarbonate fibers all may be used to reinforce the molded product. Fillers such as chalk, talcum, quartz power and ground shale, kaoline, lime spar, dolomite, mica, heavy spar, kieselguhr and aluminas also may be used. Other standard auxiliaries and additives which may be used with the epoxy polymer of the invention include, for example, organic and inorganic pigments, dyes, lubricants and release agents, thixotropizing agent, UV-absorbers, and shrinkage-reducing additives.

DETAILED DESCRIPTION OF THE INVENTION

In accord with this invention, mesogenic groups in various forms are used to modify polymers for polymeric vehicles thereby providing films, some of which are transparent, with desired characteristics. The polymeric vehicle comprises a modified polymer in the range of from about 100 to about 35 weight percent based upon the weight of the polymeric vehicle, and unmodified polymers and/or cross-linking resins in the range of from about 0 to about 65 weight percent based upon the polymeric vehicle. The modified polymer may be the diglycidyl ether of compounds having formulas (1), (2), (3) or mixtures thereof, e.g. compound (5) alone or the modified polymer may be another type of an epoxy polymer or an acrylic polymer or a polyester polymer to which mesogenic groups are covalently bound such that the coating binder contains from about 5 to about 50 weight percent mesogenic groups, based upon the weight of the modified polymer. The mesogenic groups are selected from the group consisting of I. 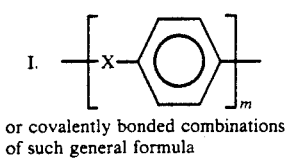

or covalently bonded combinations of such general formula

II. 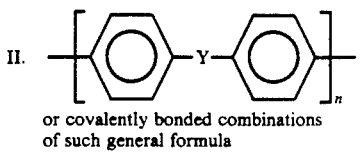

or covalently bonded combinations of such general formula

III. 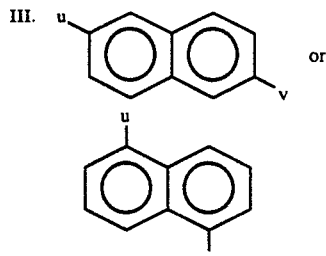

or covalently bonded combinations of such general formula

IV. Combinations of I, II, and 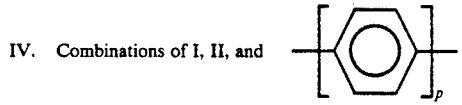

or covalently bonded combinations selected from the group consisting of the formulas I, II and

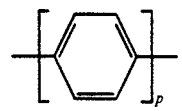

V. Combinations of III and 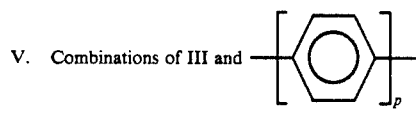

wherein X = 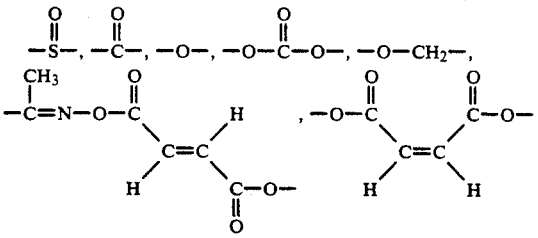

Y = X or 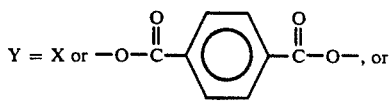

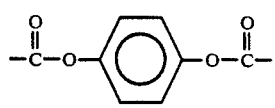

v = 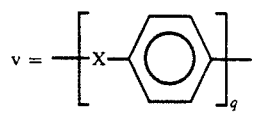

u = X m = an integer from 2 to 8;
n = 1 or 2;
p = an integer from 1 to 4; and
q = an integer from 1 to 3.

An important aspect of the invention is where the mesogenic groups have the general formula

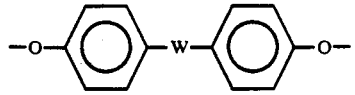

wherein W is selected from the group consisting of

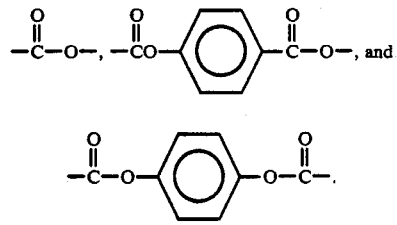

The mesogenic groups may be reacted with the polymer as seen in the examples.

When one of the reactive constituents of the mesogenic groups are not reacted with the polymer, they are terminated by —H, —CN, —COOR, —OOCR and —OR wherein R is H, alkyl (which is straight chained or branched) having 1 to 12 carbon atoms or aryl such as having from 6 to 12 carbon atoms.

The polymeric vehicle which includes a modified epoxy polymer provides a coating binder having a Tg not greater than about 180° C. as measured by Differential Scanning Colorimetry (DSC) (or not greater than 60° C. if the polymeric vehicle includes a modified acrylic or polyester polymer); and, at a thickness of about 1 mil, the coating binder has a pencil hardness of at least about "H" and a reverse impact resistance of at least about 30 inch-pounds. Films which include coating binder generally will range from about 0.05 mil to about 50 mil in thickness, but hardness and impact resistance may vary with the thickness of the film; hence hardness and impact resistance are described at a thickness of about 1 mil.

An important aspect of the invention is when the modified polymer is cross-linked. It may be cross-linked with a cross-linking resin selected from the group consisting of a di or polyamine, aminoplast resins, polyisocyanate resins, and mixtures thereof; melamine resins are a sub-class of aminoplast resins; optionally, the isocyanate groups of the polyisocyanate resin may be blocked with active hydrogen compounds such as alcohols, phenols, oximes and lactams. In an important embodiment an aminoplast or polyisocyanate resin cross-links a modified polymer which is a a polyol or contains pendant or terminal —COOH or —SH groups.

In one important embodiment mesogens having the general formula:

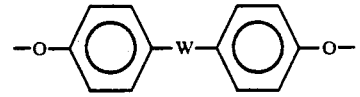

wherein W is selected from the group consisting of

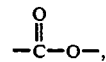

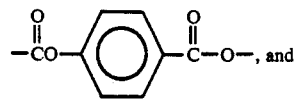

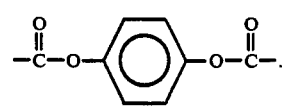

are made and then used to make a modified polymer through a reaction of any one of such mesogens or a mixture thereof with an epoxy resin, particularly DGEBPA (4). Thereafter the modified polymer is cross-linked with an amine resin such as hexakis (methyloxy-methyl) melamine (HMMM).

In another embodiment a mesogenic polyol has the general formula:

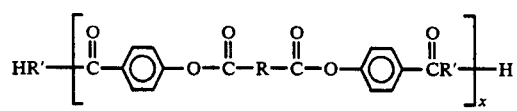

Wherein, x = 1 to 10;

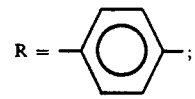

$R' = O(CH_2)_nO$, $O[(CH_2)_nO]_m$,

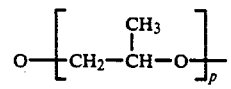

{O[(CH$_2$)$_5$COO]$_p$R''''}$_2$, or
O[R''OOCR'''COO]$_p$R''O;

R'' and R'''' = a aliphatic or cycloaliphatic radical having 12 carbon atoms or less;

R''' = aromatic radical having 10 carbon atoms or less,
cycloaliphatic radical having 12 carbon atoms or less,
or an aliphatic radical having 36 carbon atoms or less;
n = 5 to 16; m = 2 to 200; and p = 1 to 20.

An important aspect of this invention is the synthesis of the mesogens having the general formula

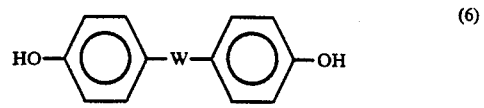

wherein W is selected from the group consisting of

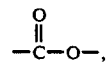

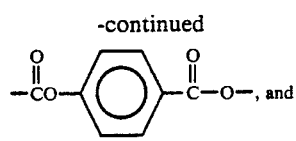

the reaction of hydroquinone with parahydroxybenzoic acid in an aromatic solvent such as benzene or an alkyl benzene as follows:

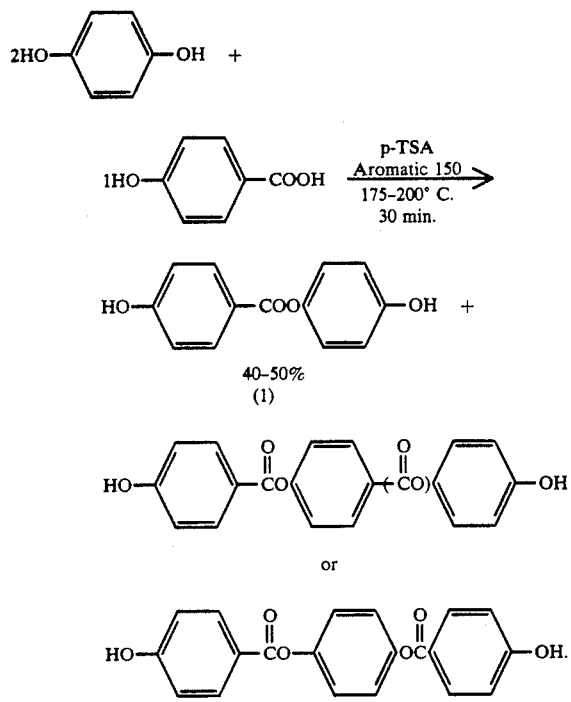

An important aspect of this invention is the use of these mesogens (6) to provide a modified polymer which is a reaction of the mesogen with an epoxide polymer such as DGEBPA which modified polymer may or may not be cross-linked. The uncross-linked modified polymer may provide a film or the modified polymer may be cross-linked to provide a film. Cross-linking may be achieved with an aminoplast such as HMMM resin. The modified polymer, cross-linked or uncross-linked provides a polymeric vehicle which when applied to a substrate provides a binder having a Tg not greater than about 180° C., a pencil hardness of at least about H, and a reverse impact resistance of at least about 30 inch lbs. at a binder thickness of about 1 mil.

Another important aspect of the invention arises in cases where the mesogenic groups are bonded to acrylic or polyester polymers by graft polymerization to prepare modified polymers. In this aspect, non-mesogenic acrylic and polyester polymers containing reactive groups such as —COOH and —OH are synthesized. The reactive groups serve as sites for grafting.

Especially preferred are grafting sites consisting of —COOH groups. Acrylic polymers containing such groups can be prepared by including —COOH functional monomers such as (meth)acrylic acid among the monomers used to prepare the acrylic monomer. Polyester resins with —COOH groups can be synthesized by using an excess of polyacid monomers over polyol monomers. Alternatively, —OH functional acrylic and polyester polymers can be provided with —COOH functional groups by reacting them with spacers such as diacids such as adipic, isophthalic or terephthalic acids or with cyclic anhydrides such as phthalic, succinic or maleic anhydrides. It is advantageous in some circumstances to convert —OH groups to —COOH groups because some reactants graft more readily to —COOH groups.

p-Hydroxybenzoic acid, PHBA, is a commonly used component of the mesogenic group in modified polymers. It may be grafted to acrylic or polyester polymers having —OH or —COOH groups; the latter are preferred. A typical grafting process is shown in FIG. 1. In this case the mesogenic groups are grafted onto the polymer to form the modified polymer are oligomeric PHBA having the general formula:

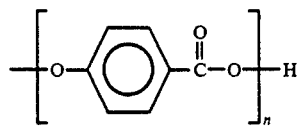

where n=2 to 8 and preferably the number average degree of polymerization of graft segments is between about 2.0 to about 6.0. See Tables 29 a–h for mesogenic examples. See Tables 29 a–c (Mono-functional Derivates), 29 d–g (Di-Functional Derivates), 29 h (Miscellaneous Derivatives) for a description of specific mesogenic groups of the invention. In Table 29 one or both open bonds of the difunctional mesogenic groups may be bonded to the modified polymer. If only one is bonded to the polymer, the other functional end may be bonded to —H or —R$_1$, where R$_1$ is a C$_1$ to C$_{12}$ alkyl group.

The modified polymer may comprise the entire polymeric vehicle, it may be blended with other polymers and/or with cross-linking resins, or it may be cross-linked by substances to which the film is exposed after application. In cases where the modified polymer is not cross-linked, it should have a number average molecular weight ($\overline{M}_n$) above about 10,000 for modified acrylic polymers and about 7,000 for modified polyester polymers. Preferred ranges are about 15,000 to 10$^6$ for acrylics and about 10,000 to 10$^5$ for polyesters. When the modified polymers undergo chemical reactions after application they may have lower $\overline{M}_n$. Preferred ranges of $\overline{M}_n$ are from about 1,000 to 50,000 for cross-linkable modified acrylic copolymers and about 500 to 20,000 for cross-linkable modified polyester copolymers. Crosslinking is effective for baked and non-baked films.

If the film is to be baked, the modified polymer and cross-linking resin, such as aminoplasts and blocked isocyanates, may be combined as components of the coating formulation. Reaction of the modified polymer and such cross-linking resins is normally very slow until the coating is applied and baked. When highly reactive cross-linking resins such a polyisocyanate resins are used, it is usually desirable to mix the components within a few hours of the time of application. Such coatings require little or no baking. Cross-linking may also be effected by exposure of the film to reactants, such as oxygen, after application; in such cases baking is optional.

The following examples set forth methods of imparting the desired characteristics to polymeric binders and to films. In these examples the properties of coatings containing modified polymers are compared to those containing similar non-modified polymers in order to demonstrate the improvements of the invention: 1) a lowered solution viscosity, 2) a hard, adherent, flexible film having excellent impact resistance and 3) greatly reduced dry-to-touch time in the case of air-dried coatings.

EXAMPLE 1

A. Preparation of

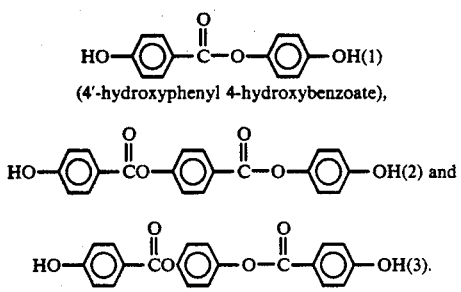

(4'-hydroxyphenyl 4-hydroxybenzoate),

A 500-mL three-neck round bottom flask was equipped with mechanical stirrer, Dean-Stark trap, condenser, thermometer and $N_2$ inlet. Hydroquinone (143.0 g, 1.30 mol), p-hydroxybenzoic acid (89.7 g, 0.65 mol), p-toluene sulfonic acid (0.32 g) and Aromatic 150 (a mixed alkyl benzene solvent commercially available from Exxon Chemical Company) (16 g) were charged into the flask. The mixture was heated (under $N_2$) to 200° C.; $H_2O$ began azeotroping and collecting in the Dean-Stark trap at 175° C. The temperature was held at 200° C. until the theoretical water of reaction was collected (about 30 min). The hot product was poured into a steel can and allowed to cool. The solidified product was ground into a powder and dissolved in 500–600 mL of hot MeOH. The solution was filtered while hot to remove insoluble by-products 2 and/or 3.

A large volume of water (about 3000 mL) was added to the MeOH solution to precipitate the product (1); (2) and/or (3) being previously separated by hot filtration. The product (1) was filtered and dissolved in MeOH and the precipitation process was repeated twice. The product was dried for 2 h at 100° C. and then overnight under vacuum at room temperature. Yield of (1) was 60 g (40% yield). mp 241°–243° C. (lit. 245°C[6]). $^1$H NMR ($Me_2SO-d_6$) 10.45 (s, 1H), 9.40 (s, 1H), 7.95 (d, 2H, j=8.4), 6.85 (m, 6H). Anal calcd for $C_{13}H_{10}O_4$: C, 67.82; H, 4.38; O, 27.78. Found: C, 67.66; H,4.43; 0, 27.35.

The by-product was washed with hot MeOH, dried and yielded 48 g of (2 and/or 3), mp (DSC) 327°–330° C. I.R. (KBr); 3250 $cm^{-1}$ (OH), 1650 $cm^{-1}$ (C=O), 1600 $cm^{-1}$ (phenyl). Anal. calcd for $C_{20}H_{14}O_6$: C, 68.56; H, 4.03; 0, 27.40. Found: C, 68.55: H, 4.01; O, 26.78.

B. Preparation of Resins And Coatings By Reacting A Diepoxy Resin With The Mesogens of Example 1A.

The diepoxies used were DER 343 (Dow) a diglycidyl ether of Bisphenol-A (DGEBPA) (Formula 3) where $\bar{n} \approx 0.1$ (determined by titration of epoxide groups). DER 343 contains a proprietary catalyst which selectively catalyzes the phenol-epoxide reaction. Resins based on Araldite RD-2 (Ciba-Geigy, the diglycidyl ether of 1,4-butanediol (DGE-1,4-BD), eq. wt.=128) were also investigated. Triphenylphosphine was used as a ring opening catalyst for reactions with RD-2. The mesogen (1) prepared is described in Example 1, Part A. Controls were prepared by substituting Bisphenol-A (4,'-isopropylidenediphenol or "Bis A") for (1) (on an equal molar basis) in the formulations.

The formulations of the polymers prepared is shown in Table 1.

TABLE 1

Polymers Prepared - mol ratios of diphenol/epoxy are given.

| (1)/DGEBPA | Bis.-A/DGEBPA |
|---|---|
| 1/1 | 1/1 |
| 3/2 | 3/2 |
| 1/2 | 1/2 |
| (1)/DGE-1,4-BD | Bis.-A/DGE-1,4-BD |
| 1/1 | 1/1 |
| 2/3 | 2/3 | i. Synthesis of Diphenol (4'-hydroxyphenyl 4-hydroxybenzoate or Bis A)/DGEBPA = 1/1 to form a coating.

The 1/1 materials were prepared as a lacquer directly on a Bonderite 1000 steel panels. The Diphenol and DGEBPA were combined in a molar ratio of 1.04:1. The mixture containing 4'-hydroxyphenyl 4-hydroxybenzoate (1) forms a smooth/fine paste. This was obtained by mixing with a vortex mixer. Excellent wetting of (1) by the epoxy is obtained. In the case of the Bisphenol-A control, a small amount of methylisobutyl ketone (MIBK) is necessary to dissolve the Bisphenol-A in the epoxy. The mixtures were applied to Bondrite 1000 steel panels using a 2 mil wire wound draw-down bar and placed in a convection oven at 200° C. for 1 hr. The cured films were 1.5 mil thick and were transparent.

ii. Synthesis of 4'-hydroxyphenyl 4-hydroxybenzoate (1)/DGEBPA = 3/2

A 50-ml round bottom flask was equipped with thermometer, $N_2$ and magnetic stirrer. 4'-hydroxyphenyl 4-hydroxybenzoate (1) (9.67 g, 0.042 mol), DGEBPA (10.47 g, 0.028 mol) and xylene (2 g) were charged into the flask. The mixture was heated to 175° C. for 1.65 h. (1) takes about 10 min at 175° C. to completely dissolve. Extent of reaction was 99% (determined by titration of epoxy group with 0.104N HBr in acetic acid).

The reaction with Bisphenol-A was carried out in the same manner - total reaction time=2 hr (99% extent reaction).

iii. Synthesis of 4'-hydroxyphenyl 4-hydroxybenzoate (1)/DGEBPA ½

A 50-mL round-bottom flask was equipped as described above. 4'-hydroxyphenyl 4-hydroxybenzoate (1) (3.57 g, 0.016 mol), DGEBPA (11.59 g, 0.032 mol) and xylene (1.5) were charged into the flask. The mixture was heated to 175° C. for about 5 min. Final epoxy eq. wt.=520 (theo eq. wt.=488).

The Bisphenol-A based resin was prepared in the same way - total reaction time=10 min; epoxy eq. wt.=503.

iv. Synthesis of 4'-hydroxyphenyl 4-hydroxybenzoate (1)/DGE-1,4-BD = ⅔

A 50-mL round-bottom flask was equipped as described above. 4'-hydroxyphenyl 4-hydroxybenzoate (1) (9.21 g, 0.040 mol)DGE-1,4-BD (15.36 g, 0.060 mol), triphenylphosphine (0.025 g) and xylene (1.25 g) were charged into the flask and the mixture was heated to 175° C. for 45 min. Epoxy eq. wt. of product=774 (theoret. eq. wt.=614).

For the reaction with Bisphenol-A; reaction time −1 hr at 175° C. Epoxy eq. wt.=500.

v. Synthesis of 4'-hydroxyphenyl 4-hydroxybenzoate (1)/DGE-1,4-BD=1/1

4'-hydroxyphenyl 4-hydroxybenzoate (1) (0.924 g, 0.0040 mol), DGE-1,4-BD (1.026 g, 0.0040 mol) and triphenylphosphine (0.002 g) were placed in a 15 mL vial. The mixture was heated under nitrogen atmosphere at 175° C. for 1 h (95% reaction based on epoxy titration).

vi. Syntheses of the diglycidyl ether of 4'-hydroxyphenyl 4-hydroxybenzoate

A three-neck 50 mL flask was equipped with thermometer, magnetic stirrer, addition funnel and condenser. 4'-hydroxyphenyl 4-hydroxybenzoate (1) (1.40 g, 6.1×10$^{-3}$ mol) epichlorohydrin (5.64 g, 0.061 mol) and dioxane (5.6 g) were added to the flask. Aqueous NaOH (2.23 g of 24% NaOH solution) was added to the addition funnel. The mixture was heated to reflux. The NaOH solution was dripped into the mixture over 3 h while the mixture was kept at reflux temperature (90°-100° C.). The mixture was held at 90° C. for 1 additional hour. 10 mL of tetrahydrofuran (THF) was added to the mixture and the mixture was filtered. The solvent was removed under vacuum. 10 mL of THF was added to the resinous product and the solution was dried with MgSO$_4$, filtered and the solvent removed under vacuum at 80° C. for 1 h. 1.7 g (82% yield) of light yellow, clear viscous product was obtained. I.R. 3400 cm$^{-1}$ (OH), 1710 cm$^{-1}$ (C=O), 1 cm$^{-1}$ (phenyl), 915 cm$^{-1}$ (epoxide). Epoxy equivalent wt.=230 (determined by titration with 0.104N HBr in acetic acid). The resin crystallizes upon standing overnight.

A sample of the epoxy was mixed with triethylenetetramine (very roughly about 50:50) and cured on a glass slide at 120° C. for 39 min. The cured film has a Tukon hardness of 25 knoops. The sample also cures to a hard film at room temperature.

C. Results and Discussion For Example 1

Table 2 shows the film properties of the 1/1 diphenol/DGEBPA based coatings. The film properties of the Bisphenol-A based coatings are very poor—the film being very brittle. The mesogen based coating has excellent impact properties as well as excellent chemical and corrosion resistance The Tg of the mesogen based coating is about 20° C. higher than the Bisphenol-A based coating The Bisphenol-A based coating is soluble in THF and has a $\overline{M}_n$ of about 5500. The mesogen based coating on the other hand is party insoluble in THF—it breaks up into small swollen fragments.

The insolubility of the mesogen based coating suggests that the film is somewhat cross-linked. While not intending to be bound by any theory, a possible explanation is based on the solubility and mp of 4'-hydroxyphenyl 4-hydroxybenzoate (1). 4'-hydroxyphenyl 4-hydroxybenzoate (1)/DGEBPA mixture is heterogeneous when applied to the panel. It takes about 5-10 min. at 200° C. for 4'-hydroxyphenyl 4-hydroxybenzoate (1) to dissolve (for the coating to become clear). During this time some reaction between epoxide groups and aliphatic OH groups on the epoxy backbone may take place causing some branching or cross-linking to occur before or during reaction of the the epoxy with the phenolic mesogen. The OH's of 4'-hydroxyphenyl 4-hydroxybenzoate (1) may also be less reactive toward the ring opening reaction compared to Bisphenol-A. The differences in the Tg's and film properties between 4'-hydroxyphenyl 4-hydroxybenzoate (1) and Bisphenol-A based coatings thus may be due to structural differences of the diphenols and/or differences in the structure of the polymer backbone caused by branching or cross-linking.

TABLE 2

| Film properties of 1/1 diphenol/DGEBPA films. | | | | |
|---|---|---|---|---|
| Diphenol | Tg | $\overline{M}_n$ | Rev. Impact | Tukon Hard. |
| 4'-hydroxyphenyl 4-hydroxybenzoate (1) | 104° C. | * | >160 in-lb | 13 Knoops |
| Bis.-A | 83° | 5460 | <5 | 12 |

Tests on 4'-hydroxyphenyl 4-hydroxybenzoate mesogen based coating

| Test | | Results |
|---|---|---|
| Salt Spray - (300 hr) | | |
| Blistering | ASTM | No Effect |
| Rusting | ASTM | No Effect |
| Humidity - (300 hr) | | |
| Blistering | ASTM | No Effect |
| Rusting | ASTM | No Effect |
| Test | | Results |
| Chemical Resistance | | |
| HCL - 10% - (300 hr) | | |
| Blistering | ASTM | No Effect |
| Color change | Score | No Effect |
| Gloss change | Score | No Effect |
| Softening (1 day recovery) | Score | No Effect |
| NaOH - 10% - (300 hr) | | |
| Blistering | ASTM | No Effect |
| Color change | Score | Trace |
| Gloss change | Score | Trace |
| Softening | Score | Very slight |
| Softening (1 day recovery) | Score | Excellent |
| MEK (methyl-ethyl) ketone) Rubs | Cycles | 45 |

Table 3 shows the Tg and size exclusion chromatography (SEC), polydispersity index $$(PDI) = \frac{Mw}{Mn}$$

wherein $\overline{M}_n$ is number average molecular weight and $\overline{M}_w$ = weight average molecular weight) data measured for the 2/1 DGEBPA/diphenol epoxies. Tg's of the resins could not be obtained because the resin solutions gelled when heated to remove solvent. The mol. wt. and also the polydispersity index (PDI) of the mesogen based epoxy is higher than that of the Bisphenol-A based epoxy. The differences in Tg and mol. wt. and PDI may be due to the structural differences of the diphenols or differences in the network structure (branching) as stated previously. The difference in mol. wt. and PDI suggests that some branching is occurring during the synthesis of the mesogen based polymer.

TABLE 3

| TG and SEC data for 2/1 DGEBPA/diphenol based epoxies.* | | | |
|---|---|---|---|
| Diphenol | Tg (film*) | $\overline{M}_n$ | PDI |
| (1) | 87° | 920 | 5.8 |

TABLE 3-continued

| TG and SEC data for 2/1 DGEBPA/diphenol based epoxies.* | | | |
|---|---|---|---|
| Diphenol | Tg (film*) | $\overline{M}n$ | PDI |
| Bis.-A | 79° | 690 | 3.4 |

*cured with 10% triethylenetetramine, 120° C./30 min

Table 4 shows the cured film properties cured 2/1 DGEBPA diphenol epoxies. The modified epoxies were cured with triethylenetetramine at 120° C. for 30 min. All films (mesogen and Bisphenol-A based) display excellent reverse impact strength when cured with 7–15 wt. % amine. The mesogen based films are about 20% harder than the Bisphenol-A based films. All films have excellent acetone rub resistance.

TABLE 4

| Cured film properties of 2/1 DGEBPA/diphenol based epoxies. | | | | |
|---|---|---|---|---|
| Diphenol | Wt. % Amine* | Rev. Impact[1] | Tukon Hard.[2] | Acetone Rubs[3] |
| (1) | 7% | >160 | 15.5 | >200 |
| (1) | 10% | >160 | 17.5 | >200 |
| (1) | 15% | >160 | 17 | >200 |
| Bis.-A | 4% | <10 | 13.5 | <10 |
| Bis.-A | 7% | >160 | 14.5 | >200 |
| Bis.-A | 10% | >160 | 14 | >200 |
| Bis.-A | 15% | >160 | 13.5 | >200 |

*cured with triethylenetetramine at 120° C. for 30 min.

1. Reverse Impact Strength

Reverse impact strength was determined by ASTM method D2794. A 4 lb. steel cylinder with a rounded head (⅝" diameter) is dropped through a vertical guide tube onto the coated steel panel, supported film side down on a steel support Ring. Impact strength is defined as the maximum height (measured in in-lb) which the weight is dropped which does not crack the coating.

2. Tukon Hardness

Film hardness was determined using a Wilson model MO Tukon hardness tester—ASTM method D384. A diamond shaped scribe is mechanically lowered onto the film for a set time (−30 sec.). The scribe rests on the film with a 25 g load. The length of the indentation made on the film is measured via a calibrated grid in the optics of a viewing microscope. The length of the indentation on the film is converted using a standard, recognized table to Knoop hardness units.

3. Acetone Resistance

Acetone resistance of the cured films was determined by rubbing a acetone saturated Kim-Wipe over the surface of the film. The number of rubs to mar to dissolve the film is reported. A value of >200 means that no effect was observed after 200+rubs.

The acetone rub resistance is a qualitative measure of the degree of cross-linking of a polymer film. A low number of rubs (< TM 20) indicates that the film is not fully cured. A value of >200 indicates that the film is fully cured.

Table 5 shows the DSC and SEC data of the 3/2 diphenol/DGEBPA based polymers. The Tg of the 4'-hydroxyphenyl 4-hydroxybenzoate mesogen based polymer is considerably higher (20° C.) than that of the polymer based on Bisphenol-A. The 4'-hydroxyphenyl 4-hydroxybenzoate mesogen based polymer is about 40% higher in mol. wt. than the Bisphenol-A based polymer. These differences in Tg and mol. wt. may due to the structural differences of the diphenols or differences in the network structure (branching) as stated previously. The 4'-hydroxyphenyl 4-hydroxybenzoate mesogen takes about 10 min to dissolve when the reaction temperature reaches 175° C. Some intramolecular reactions of epoxide and aliphatic OH groups of the DGEBPA resin may occur before (1) is dissolved.

Table 6 shows the cured film properties of the polymers. The polymers were cured with HMMM resin. All films (both 4'-hydroxyphenyl 4-hydroxybenzoate (1) and Bisphenol-A based) are quite brittle as reflected in the impact properties. All films have good hardness. The 4'-hydroxyphenyl 4-hydroxybenzoate mesogen based films are 20-25% harder than the corresponding Bisphenol-A based films.

TABLE 5

| DSC and SEC data of 3/2 diphenol/DGEBPA. | | | |
|---|---|---|---|
| Diphenol | Tg (film) | $\overline{M}n$ | PDI |
| (1) | 86° | 1930 | 3.1 |
| Bis.-A | 65° | 1180 | 3.0 |

TABLE 6

| Film properties of 3/2 diphenol/DGEBPA. | | | | | |
|---|---|---|---|---|---|
| Di-phenol | (Resin/HMMM; cure schedule; wt. % p-TSA) | | Rev. Imp. | Tukon Hard. | Acetone Rubs |
| (1) | 75/25 | 149° C./30 min 0.5% | <10 | 22 | >200 |
| Bis.-A | 75/25 | 149° C./30 min 0.5% | <10 | 18 | >200 |
| (1) | 75/25 | 190° C./30 min 0.5% | <10 | 23 | >200 |
| Bis.-A | 75/25 | 190° C./30 min 0.5% | <10 | 18 | >200 |
| (1) | 85/15 | 190° C./30 min 0% | <10 | 18 | >200 |
| Bis.-A | 85/15 | 190° C./30 min 0% | <10 | 14 | <5 |
| (1) | 85/15 | 190° C./60 min 0% | <10 | 18 | >200 |
| Bis.-A | 85/15 | 190° C./60 min 0% | <10 | 14 | <5 |

Table 7 shows the physical properties of the 1/1 4'-hydroxyphenyl 4-hydroxybenzoate mesogen/DGE-1,4-BD polymer. This polymer was prepared to see if it would be liquid crystalline since it is made from alternating mesogenic and flexible spacer (DGE-1,4-BD) groups. The resin shows no observable texture under a polarizing microscope; it appears to be completely amorphous. From the large PDI it is apparent that some branching occurred during synthesis. A significant amount of branching would decrease the ability of the oligomer to form the mesophase.

TABLE 7

| Physical properties of 1/1 (1)/DGE-1,4-BD polymer. | | | |
|---|---|---|---|
| Tg | $\overline{M}n$ | PDI | Optical Texture |
| 20° | 2630 | 9.9 | amorphous |

Table 8 shows the resin and film properties of the 3/2DGE-1,4-BD/diphenol. The mol. wt. of the 4'-hydroxyphenyl 4-hydroxybenzoate mesogen based polymer is substantially higher than the Bisphenol-A based polymer. The resins were cured with 25 wt. % Polyamide 840 (Ciba-Geigy) at 120° C. for 30 min. Both films had excellent reverse impact strength but were very soft.

TABLE 8

| Resin and film properties of 3/2 DGE-1,4-BD/diphenol.* | | | | | |
|---|---|---|---|---|---|
| Diphenol | $\overline{M}n$ | PDI | Tg (cured) | Rev. Imp. | Tukon Hard. | Acetone Rubs |
| (1) | 2300 | 17.9 | 23° | >160 | 1.5 | >200 |

TABLE 8-continued

| | | | Resin and film properties of 3/2 DGE-1,4-BD/diphenol.* | | | |
|---|---|---|---|---|---|---|
| Diphenol | $\overline{M_n}$ | PDI | Tg (cured) | Rev. Imp. | Tukon Hard. | Acetone Rubs |
| Bis.-A | 900 | 2.1 | 18 | >160 | >>1 | 30 |

*Resins cured with Polyamide 840 (Ciba-Geigy) at 120° C. for 30 min.

CONCLUSIONS AS TO EXAMPLE 1

The cured film properties of the mesogen based polymers are superior to those of the Bisphenol-A based polymers. Reverse impact strength of the mesogen based 1/1 diphenol/DGEBPA coating is excellent while the Bisphenol-A based coating has very poor impact strength. Films based upon the diglycidyl ether of 4'-hydroxyphenyl 4-hydroxybenzoate indicated a superior utility. In the hard coatings studied the mesogen based films have superior hardness (15-25% harder than Bisphenol-A based films).

EXAMPLE 2

This example concerns model alkyd resins made by a synthetic procedure. The example involves grafting oligomeric esters of p-hydroxybenzoic acid (PHBA) or of PHBA/terephthalic acid (TPA) to alkyd resins so that liquid crystalline phases are formed. Here the objective is to demonstrate the usefulness of L-C alkyds.

Materials

Linoleic acid (Emersol 315, Emery Ind. Inc., equivalent weight 288) was dried with anhydrous $Na_2SO_4$. Pyridine (Aldrich) was distilled and dried with anhydrous $Na_2SO_4$. All other materials (Aldrich) were used as received.

Synthesis of Grafted Model Alkyds G1-G5

Synthesis of grafted PHBA-modified alkyds is outlined in FIG. 1.

(A.) Preparation of unmodified alkyd U1. A low molecular weight model alkyd, U1, with 55% oil length and 22% OH excess was prepared from 25.00 g (0.0868 mol) of linoleic acid, 10.70 g (0.0722 mol) of phthalic anhydride, and 12.61 g (0.094 mol) of trimethylolpropane using the DCC-p-TSA process described by Kangas, S. and Jones, F. N., "Model alkyd resins for higher-solids coatings, I", *J. Coat. Technol.*, 59(744), 89 (1987). DCC is dicyclohexyl carbodiimide. Yield was 85%. The OH value was 56 mg-KOH/g determined by the phthalic anhydride/pyridine method.

(B1.) Modification with succinic anhydride. Alkyd U1 was heated with succinic anhydride (one mol per equiv OH) in pyridine at 80° C. for 12 hr. The solution was concentrated; the residue was dissolved in $CH_2Cl_2$ and washed with 10% aq. HCl. The $CH_2Cl_2$ layer was concentrated and the residue was vacuum dried at 80° C. Yield of resin was above 90%; acid number was 64 mg-KOH/g.

(B2.) Modification with terephthalic acid (TPA). A solution of 10.0 g (0.010 equiv) of alkyd U1, 8.51 g (0.050 mol) of terephthalic acid (TPA) 2.27 g (0.011 mol) of DCC and 0.11 g of p-toluenesulfonic acid (p-TSA) in 150 ml of pyridine was stirred at 25° C. for 12 hr. The mixture was filtered to remove DCU (dimethylcyclohexylurea) and excess TPA. The filtrate was concentrated, dissolved in $CH_2Cl_2$, washed with 10% aq. HCl and concentrated as above. Traces of crystalline material were removed by dissolving the residue in 1/1 pentane/ethyl acetate, cooling in a freezer, filtering, reconcentrating and vacuum drying at 80° C. Yield was 9.62 g of resin; acid number was 62 mg-KOH/g.

(C.) Grafting to form alkyds G1-G5. The intermediate step of reacting alkyd U1 with succinic anhydride or with TPA is desirable to improve grafting efficiency. This step converts —OH groups of U1 to —COOH groups; grafting to —COOH groups is more efficient. The succinic anhydride modified alkyd was grafted or covalently bonded with PHBA using the DCC-p-TSA/pyridine process. Weight ratios (PHBA/alkyd) of 0.1, 0.2, 0.3 and 0.5 gave alkyds G1-G4 respectively. For example, the synthesis on alkyd G2 is described:

A solution of 10.0 g (0.0114 equiv) of carboxyl-terminated model alkyd (prepared as described in B1. above), 2.0 g (0.0145 mol) of PHBA, 3.14 g (0.0152 mol) of DCC, and 0.16 g of p-TSA in 120 ml of pyridine was stirred at 25° C. for 12 hrs. The product (10.2 g, 85% yield) was isolated essentially as described immediately above in the TPA reaction.

TPA modified alkyd prepared as described in B2 was covalently bonded by a similar process using a weight ratio (PHBA/alkyd) of 0.5 to give alkyd G5. Modification with TPA has the additional advantage of putting half the structure needed for liquid crystal formation into place.

Synthesis of "Random" Model Alkyds R1-R3

A series of random model alkyds R1, R2 and R3 containing 15%, 22% and 27% by weight in the feed were prepared from linoleic acid, phthalic anhydride, trimethylolpropane, and PHBA in a single step by the DCC-p-TSA process. These weight percents correspond roughly to the weight percents of PHBA actually incorporated in alkyds G2, G3 and G4, respectively. For example, preparation of R3 is described:

A solution of 5.5 g (0.0190 mol) of linoleic acid, 2.54 g (0.017 mol) of phthalic anhydride, 2.91 g (0.022 mol) of trimethylolpropane, 4 g (0.029 mol) of PHBA, 12.24 g (0.060 mol) of DCC, and 0.612 g of p-TSA in 200 ml of anhydrous pyridine were mixed in a 250 ml flask for 12 hrs. at 25° C. Alkyd R3 was isolated essentially as described above in the TPA reaction.

Alkyd Structure Characterization $^1$H-NMR spectra were determined at 34° C. using a Varian Associates EM 390 NMR spectrometer with $Me_4Si$ as internal standard. IR spectra were recorded on a Perkin-Elmer 137 spectrophotometer using a 20 weight percent solution in $CH_2Cl_2$.

Differential scanning calorimetry (DSC) was effected with a du Pont model 990 thermal analyzer at a heating rate of 20° C./min using samples that had been vacuum dried at 80° C. to constant weight. Tg was assigned as the onset of the endothermic inflection. Clearing points ($T_{cl}$) of L-C phases were assigned as the maxima of the endothermic peaks.

Equivalent weight per carboxyl group was determined by titration of pyridine solution with $KOH/CH_3OH$ to the phenolphthalein end point.

Number average molecular weight ($\overline{M}_n$), weight average molecular weight ($\overline{M}_w$), and polydispersity index (PDI=$\overline{M}_w/\overline{M}_n$) were measured by gel permeation chromatography (GPC) in tetrahydrofuran using a Waters model 510 pump, a R401 refractive index detector and a model M730 data module; columns were Ultrastyragel 100 A, 500 A, 103 A, and 104 A. Monodisperse polystyrene calibration standards were used.

Optical textures were examined with a Leitz D-6330 polarizing microscope equipped with a Reichert hot stage.

Grafting efficiency (GE%) and average number of PHBA units per COOH were estimated from equivalent weight difference as described in Chen, D. S. and Jones, F. N., "Graft-copolymers of p-hydroxylbenzoic acid, Part I, A general method for grafting mesogenic groups to oliogmers", *J. Polym. Sci., Polym. Chem. Ed.*, Vol. 25, pg. 1109-1125 (1987).

Measurement of Viscosity and Tests of Films Properties

Solution viscosity was measured in xylene using an ICI cone and plate viscometer at 25° C. Films were prepared by dissolving or dispersing resins and driers in xylene and casting films on untreated rolled steel panels by a casting bar to give the dry thickness of 0.5 ml.

Dry-to-touch time was measured according to ASTM D1640. Film properties were measured after 7 days of drying at ambient temperature. Reverse impact resistance and pencil hardness were measured according to ASTM D2794 and D3363 respectively; resistance to acetone was measured by the number of double rubs to remove trace of film with paper tissue after the dropping of acetone on the dry film. Extractability was measured by subjecting cured films to 8 hr. in a Soxhlet extractor using tetrahydrofuran.

The equivalent weight per carboxyl, $\overline{M}_n$, $\overline{M}_w$, PDI, and number average PHBA units per carboxyl of the control alkyd and the PHBA-grafted alkyds are shown in Table 9. As PHBA content increases equivalent weight, $\overline{M}_n$, and $\overline{M}_w$ increase in proportion to the mass of PHBA grafted but no more; PDI remains nearly constant. These results indicate that little or no coupling of molecules occurs during grafting. Data for "random" alkyds R1-R3 are shown in Table 10.

TABLE 9

| Characterization of ungrafted alkyd U1 and PHBA-grafted G1—G4: | | | | | |
|---|---|---|---|---|---|
| | U1 | G1 | G2 | G3 | G4 |
| wt ratio in feed PHBA/oligomer | — | 0.1 | 0.2 | 0.3 | 0.5 |
| Eq. wt. per COOH (g/eq.) | 876* | 916 | 1014 | 1065 | 1080 |
| wt % of PHBA in resin | — | 8.3 | 14.5 | 19.4 | 28.4 |
| GE % | — | 90 | 89 | 85 | 77 |
| units of PHBA GRAFTED PER COOH | — | 0.4 | 1.15 | 1.58 | 1.96 |
| $\overline{M}_n$ | 1425** | 1460 | 1582 | 1717 | 1935 |
| $\overline{M}_w$ | 2086** | 2287 | 2418 | 2689 | 2910 |
| PDI | 1.46 | 1.57 | 1.53 | 1.57 | 1.50 |
| Tg (C) | −29 | −24 | −20 | −15 | −10 |
| $T_{cl}$ (C)*** | — | — | — | — | 190 |

*After grafting with succinic anhydride.
**Before grafting with succinic anhydride.
***Clearing temperature.

TABLE 10

| Properties of "random" alkyds: | | | |
|---|---|---|---|
| | R1 | R2 | R3 |
| wt % of PHBA in feed | 15 | 22 | 27 |
| $\overline{M}_n$ | 1650 | 1720 | 1600 |
| $\overline{M}_w$ | 2772 | 2597 | 2512 |
| PDI | 1.68 | 1.51 | 1.57 |
| Tg, C | −23 | −18 | −12 |

IR spectra of the PHBA grafted alkyds are characterized by two sharp peaks at 1610 and 1510 cm$^{-1}$. $^1$H-NMR spectra show complex peaks in the range of 7.0-8.0 ppm. These spectral features are characteristic of PHBA grafted polymers. IR of random alkyds R1-R3 also showed two sharp peaks at 1610 and 1510 cm$^{-1}$.

Onset Tg (by DSC) of the unmodified alkyd U1 was −29 C; PHBA-grafted alkyds G1-G5 had onset Tgs at −24°, −20°, −15°, −10°, and +17° C., respectively. DSC traces of the alkyd U1 and grafted alkyds G1-G3 were featureless except for the inflection assigned to Tg and the broad exothermic peaks due to thermal crosslinking. DSCs of alkyds G4 and T5 had sharp endothermic peaks at 190° and 225° C., respectively; these peaks are attributable to the clearing temperature ($T_{cl}$) of the L-C phases. DSC thermograms of random alkyds R1-R3 are similar to those of alkyds U1, G1, G2, and G3, no endothermic peaks appeared. Tgs of R1, R2, and R3 were −23, −18, and −12 C, respectively.

Optical textures of the dried films were examined under a polarizing microscope with a hot stage. Films of alkyds U1, G1-G3 and R1-R3 had no visible L-C phases. However, L-C (mesomorphouse) phases were clearly visible in films of alkyds G4 and G5. The L-C phase in films of alkyd G4 disappeared when the specimen was heated above 190° C. and reappeared quickly as it was cooled to around 190° C.

Viscosity and Appearance of Solutions and Dispersions

Alkyds U1, G1-G3 and R1-R3 appeared soluble in commercial xylene at all concentrations. In contrast, alkyds G4 and G5 formed stable, opaque dispersions in xylene at concentrations of 5 wt % or higher.

The relationship between viscosity and PHBA content of 70/30 (w/w) mixtures of alkyds G1-G4 and R1-R3 in xylene was investigated. Viscosity increases with increasing PHBA content for alkyds G1-G3, but it drops sharply for alkyd G4. This drop is presumably associated with the tendency of alkyd G4 to form non-aqueous dispersions. On the other hand, "random" alkyd R3, whose overall composition is similar to that of G4, has the highest viscosity in the series.

Dry Time and Film Properties

As shown in Table 11, all PHBA-grafted alkyds dried faster than unmodified alkyd U1, and drying speed increased with PHBA content. Acceleration of drying is by far the greatest for L-C alkyds G4 and G5. The latter dried very rapidly (in 5 minutes). As shown in Table 12, the drying speed of "random" alkyds R1-R3 also increased with the PHBA content, but the effect was much smaller than observed for their grafted counterparts G2-G4.

Coatings made from all alkyds had good adhesion. Films made from alkyds U1, G1-G3 and R1-R3 were glossy and transparent, while film from alkyds G4 and G5 were glossy and translucent.

As shown in Table 11, seven-day old films of PHBA-grafted alkyds G1-G5 had better reverse impact resistance, were harder, and had slightly better acetone resistance than alkyd U1. All these film properties are favored by higher PHBA content. Alkyd G4 had the best balance of properties, while alkyd G5 was the hardest.

TABLE 11

Dry-to-touch times and film properties of U1 and grafted alkyds G1–G5:

| Alkyd | U1 | G1 | G2 | G3 | G4 | G5 |
|---|---|---|---|---|---|---|
| Dry time* | 10 D | 5 D | 7 H | 5.5 H | 1 H | 5 M |
| film properties | | | | | | |
| hardness | 5 B | 3 B | 2 B | B | H | 2 H |
| reverse impact strength (in-lb) | 35 | 35 | 40 | 65 | 80 | 45 |
| crosshatch adhesion | 100% | 100% | 100% | 100% | 100% | 100% |
| resistance to acetone (rubs) | 3 | 5 | 5 | 6 | 8 | 8 |
| film appearance | GL TP | GL TP | GL TP | GL TP | GL TL | GL TL |

*dryers = 0.05% Co-naphthenate + 0.15% Zn-naphthenate by weight per resin.
D = day, H = hour, M = minute.
GL = glossy, TP = transparent, TL = translucent.

Hardness and solvent resistance of films made from "random" alkyds R1–R3 improved with increasing PHBA content (Table 12). On the other hand, impact strength decreased with increasing PHBA content.

TABLE 12

Dry-to-touch times and film properties of "random alkyds" R1—R3:

| | R1 | R2 | R3 |
|---|---|---|---|
| Dry time* | 5 H | 4.5 H | 3.5 H |
| Film Properties | | | |
| Hardness | HB | HB | H |
| reverse impact strength (in-lb) | 80 | 45 | 20 |
| crosshatch adhesion | 100% | 100% | 100% |
| Resistance to acetone (number of rubs) | 3 | 4 | 4 |
| film appearance | GL, TP | GL, TP | GL, TP |

*dryers = 0.05% Co-naphthenate + 0.15% Zn-naphthenate per resin.
H = hour, GL = Glossy, TP = Transparent.

The data of the above example indicates the improvements made in an alkyd coating and resin when mesogenic groups are covalently bonded to the alkyd.

EXAMPLE 3

This example reports use of mesogenic groups to modify acrylic polymers. The experimental approach was to prepare several series of —COOH functional acrylic copolymers in which molecular weight, Tg, and functionality were varied and then to graft p-hydroxybenzoic acid (PHBA) to the —COOH groups. The PHBA groups were the mesogenic groups which imparted the desired L-C characteristics.

Two types of L-C acrylic polymers were synthesized. In type A the PHBA was grafted to —COOH groups attached directly to methyl methacrylate/butylacrylate/methacrylic acid (MMA/BA/MAA) acrylic copolymer backbones. In type B an 8-unit flexible spacer was placed between the copolymer backbone and the PHBA. The behavior of these copolymers as film formers was investigated.

Materials

Monomers were distilled before use. Pyridine was distilled and then dried by stirring with anhydrous $Na_2SO_4$. All other reagents (Aldrich) were used as received.

Preparation of COOH-Functional Acrylic Polymers

COOH-functional acrylic polymers were prepared as substrates for grafting by radical copolymerization in toluene at 90°–100° C. under monomer starved conditions as described by R. A. Gray, J. Coat. Technol., 57, 83 (1985), using azobisisobutyronitrile (AIBN) as initiator. Substrates for Type A copolymers were composed of methyl methacrylate (MMA), butyl acrylate (BA), and acrylic acid (AA) or methacrylic acid (MAA). Substrates for Type B copolymers were composed of MMA, BA, and 2-hydroxyethyl methacrylate (HEMA); they were modified to become COOH-functional by treatment with stoichiometrically equivalent amount of succinic anhydride in pyridine at 80° C.

The following is an example for the preparation of a COOH-functional acrylic polymer of Type B:

(a). Polymerization: Toluene (57 g) was placed in a 250-ml, 3-neck flask, heated in an oil bath and stirred mechanically. A solution of 32.68 g (0.255 mol) of BA, 22.03 g (0.22 mol) of MMA, 3.25 g (0.025 mol) of HEMA, and 0.57 g of AIBN was added dropwise during 3 hr with continuous stirring. Temperature was maintained at 95° to 100° C. during addition and for 2 hr. thereafter. A solution of 0.2 g of AIBN in 10 g of toluene was added during 10 min, and the temperature was maintained for 1 hr. The solution was concentrated on a rotary evaporator and was vacuum dried at 80° C. The residue (polymer B6) had 5 mol % OH functionality (calcd), a Tg of 10° C. (calcd) and Mn of 15,400 (measured by GPC). Acrylic copolymers of type A were prepared similarly.

(b). Modification with succinic anhydride: A solution of 11.45 g (0.005 eq OH) of the above polymer and 0.50 g (0.005 mol) of succinic anhydride in 50 g of pyridine was stirred and heated at 80° C. for 12 hr. The solution was concentrated; the residue was dissolved in $CH_2Cl_2$ and washed with 10% aq. HCl. The $CH_2Cl_2$ layer was concentrated and the residue was vacuum dried at 80° C. Yield was 92%. Acid number was 24.

Grafting with PHBA

Both types of COOH-functional acrylic copolymers were grafted with PHBA in pyridine at 100° C. for 36 hr by the DCC-p-TSA process. Ratios of mol of PHBA to equiv of —COOH ("equivalent ratios") were 3.5, 5.5, and 7.0 in order to vary the length of the grafted PHBA segments. The PHBA-grafted products of Types A and B were designated GA and GB respectively. The procedure is exemplified by the grafting of succinic anhydride-modified polymer B6 at equivalent ratio of 7.0:

A solution of 11.80 g (0.005 eq COOH) of polymer B6, 4.84 g (0.035 mol) of PHBA, 7.94 g (0.0385 mol) of dicyclohexycarbodiimide (DCC), and 0.40 g of p-toluenesulfonic acid (p-TSA) in 150 g of pyridine was stirred at 100° C. for 36 hr. The mixture was filtered to remove urea of DCC (DCU) and PHBA oligomers. The filtrate was concentrated, dissolved in $CH_2Cl_2$, washed with 10% aq. HCl, and concentrated. Traces of crystalline contaminates were removed by dissolving the residue in 1:1 pentane-ethyl acetate, cooling in a freezer, filtering, reconcentrating, and vacuum drying at 80° C. Yield was 85%. The combined crystalline by-products weighed 9.40 g after vacuum drying at 80° C. to constant weight. Grafting efficiency (GE%) was estimated to be 70% indicating an average length of PHBA grafts (#PHBA/COOH) of 4.9 PHBA units.

Grafting was effected to give L-C copolymers of Types GA and GB. These types differ in that the mesogenic PHBA-grafts are attached directly to the polymer backbone of Type GA copolymers while Type GB copolymers have eight-atom flexible spacers between the polymer backbone and the mesogenic grafts. Individual copolymers were numbered as shown in Tables 13 to 19. Grafting efficiency (GE%) was determined gravimetrically. It ranged from about 85% to about 70%. As expected, GE% decreased as the COOH equivalent ratio of PHBA/acrylic increased.

Average #PHBA/COOH ratios were calculated from GE%. In order to achieve #PHBA/COOH ratios of 3±0.2, 4±0.2, and 5±0.3 it proved necessary to feed PHBA monomer in the ratio of 3.5, 5.5 and 7.0 moles, respectively, to the grafting reaction.

Structure Characterization $^1$H-NMR spectra, IR spectra, differential scanning calorimetry (DSC), optical textures under polarizing microscope, $\overline{M}_n$, $\overline{M}_w$, polydispersity index, and average #PHBA/COOH ratio were determined as described in Chen and Jones. The term "#PHBA/COOH ratio" refers to the number average degree of polymerization of PHBA graft segments actually incorporated in the graft copolymer.

X-ray spectra were recorded with a Philip wide angle diffractometer at 25° C. Samples for X-ray diffraction studies were dissolved or dispersed in acetone, cast on glass slides, and vacuum dried at 80° C. for 12 hr.

Measurement of Viscosity

Viscosity was measured using an ICI cone and plate viscometer (shear rate $10^4$ s$^{-1}$) at 25° C. Samples were dissolved or thoroughly dispersed in methylisobutylketone (MIBK) before measuring.

Observation of Solution Appearance

Samples were dissolved or dispersed thoroughly in MIBK and then put in test tubes. Appearance was observed when the test tubes were immersed in an oil bath and equilibrated at different temperatures. Optical textures of some L-C polymer dispersions were examined under polarizing microscope at 25 C.

Tests of Film Properties

Samples were dissolved or dispersed in MIBK and cast on untreated cold rolled steel panels by a casting impact strength and pencil hardness were measured according to ASTM D2794 and D3363, respectively.

Characterization of Polymer Structures

The IR spectra of the PHBA grafted acrylics have sharp peaks at 1610 cm$^{-1}$ and 1510 cm$^{-1}$ assignable to the para aromatic C-H stretching. These two peaks are characteristic of oligo-PHBA grafted polymers. They are absent in the ungrafted acrylics.

$^1$H-NMR spectra of the PHBA-grafted acrylics show multiple peaks in the range of 7.0–7.3 ppm and 8.0–8.3 ppm, assignable to the aromatic protons ortho to the OH group and to the COOH group, respectively. They are absent in the ungrafted acrylics.

Characterization of Microstructure

Polarizing microscopy, differential scanning calorimetry (DSC), and wide angle X-ray diffraction (WAXS) were used to further characterize the microstructures of the graft copolymers in the bulk phase. Results (Tables 13 and 14) were consistent with assignment of L-C microstructure to all polymers except GA21a-c.

TABLE 13

Compositions of type A acrylic substrates and type A PHBA-grafted acrylic copolymers (a). Type A acrylic substrates:
(a1). The —MAA—BA—AA—series

| # | mol fraction (MMA/BA/AA) | Tg (°C., calcd.) | $\overline{M}_n$ |
|---|---|---|---|
| A11 | 0.274/0.676/0.05 | −10 | 15,700 |
| A12 | 0.355/0.595/0.05 | 0 | 28,400 |
| A13 | 0.274/0.676/0.05 | −10 | 4,870 |
| A14 | 0.274/0.676/0.05 | −10 | 9,945 |
| A15 | 0.274/0.676/0.05 | −10 | 14,865 |
| A16 | 0.274/0.676/0.05 | −10 | 28,500 |
| A17 | 0.355/0.595/0.05 | 0 | 4,750 |
| A18 | 0.332/0.593/0.75 | 0 | 4,810 |
| A19 | 0.309/0.591/0.10 | 0 | 5,100 |
| A20 | 0.355/0.595/0.05 | 0 | 15,630 |

(a1). The —MMA—BA—MAA—series

| # | mol fraction (MMA/BA/MAA) | Tg (°C., calcd.) | $\overline{M}_n$ |
|---|---|---|---|
| A21 | 0.351/0.549/0.10 | 10 | 4,910 |
| A22 | 0.383/0.542/0.075 | 10 | 5,130 |
| A23 | 0.415/0.535/0.05 | 10 | 5,490 |

(b). Type GA PHBA-grafted acrylic copolymers:
(b1). series from —MMA—BA—AA—

| # | # PHBA/COOH | PHBA content (wt %) | Tg (°C., measured) | $T_{cl}$ | LC phase* |
|---|---|---|---|---|---|
| GA11 | 4.9 | 20.0 | −2 | 173 | smectic |
| GA12 | 5.1 | 21.0 | −4 | 175 | smectic |
| GA13 | 5.2 | 21.0 | −2 | 174 | smectic |
| GA14 | 5.0 | 20.3 | −3 | 174 | smectic |
| GA15 | 4.9 | 20.0 | −2 | 173 | smectic |
| GA16 | 5.1 | 20.7 | −4 | 174 | smectic |
| GA17 | 4.9 | 20.3 | 7 | 173 | smectic |
| GA18 | 5.2 | 29.0 | 9 | 174 | smectic |
| GA19 | 4.8 | 33.6 | 14 | 181 | smectic |
| GA20 | 4.8 | 19.8 | 4 | 174 | smectic |

(b2). Series from —MMA—BA—MAA—

| # | # PHBA/COOH | PHBA content (wt %) | $T_4$ | $T_m$ | $T_{cl}$ (°C., measured) | LC phase* |
|---|---|---|---|---|---|---|
| GA21a | 3.2 | 25.2 | 16 | 147 | — | crystal |
| GA21b | 4.1 | 30.1 | 22 | 186 | — | crystal |
| GA21c | 4.9 | 34.0 | 25 | 210 | — | crystal |
| GA22a | 3.0 | 20.3 | 15 | — | 165 | smectic |
| GA22b | 3.8 | 23.2 | 18 | — | 175 | smectic |
| GA22c | 4.8 | 27.6 | 20 | — | 184 | smectic |
| GA23a | 3.1 | 14.0 | 14 | — | 162 | smectic |
| GA23b | 4.0 | 17.4 | 15 | — | 173 | smectic |
| GA23c | 5.1 | 21.1 | 17 | — | 178 | smectic |

*according to optical texture.

TABLE 14

Compositions of type B acrylic substrates and type GB PHBA-grafted acrylic copolymers (a). Type B acrylic substrates

| # | mol fraction (MMA/BA/HEMA) | Tg (°C., calcd.) | $\overline{M}_n$ |
|---|---|---|---|
| B1 | 0.282/0.668/0.05 | −10 | 14,500 |
| B2 | 0.364/0.586/0.05 | 0 | 15,130 |
| B3 | 0.364/0.586/0.05 | 0 | 5,050 |
| B4 | 0.364/0.586/0.05 | 0 | 10,800 |
| B5 | 0.364/0.586/0.05 | 0 | 28,200 |
| B6 | 0.044/0.51/0.05 | 10 | 15,420 |

(b). Type GB PHBA-grafted acrylic substrates

| # | # PHBA/COOH | PHBA content (wt %) | Tg (°C., measured) | $T_{cl}$ | LC phase* |
|---|---|---|---|---|---|
| GB1 | 5.0 | 19.3 | −5 | 171 | smectic |
| GB2a | 4.8 | 19.0 | 4 | 174 | smectic |
| GB2b | 3.2 | 13.5 | 3 | 159 | smectic |
| GB2c | 4.1 | 16.7 | 3 | 164 | smectic |
| GB3 | 5.1 | 19.9 | 4 | 175 | smectic |

TABLE 14-continued

Compositions of type B acrylic substrates and type GB PHBA-grafted acrylic copolymers

| GB4 | 4.9 | 19.3 | 5 | 174 | smectic |
| GB5 | 5.2 | 20.2 | 5 | 174 | smectic |
| GB6 | 4.9 | 19.6 | 14 | 177 | smectic |

*according to optical texture.

The shear viscosities (shear rate $10^4$ s$^{-1}$) of MIBK solutions of three ungrafted arcylic copolymers and of a dispersion of an L-C graft copolymer derived from one of them as a function of concentration were studied. The ungrafted copolymers (B1, B2, and B6) differ only in Tg ($-10°$, $0°$, $+10°$ C., respectively); all three have $\overline{M}_n$ of about 15,000 and functionality of 5 mol %. L-C copolymer GB1 was prepared by grafting B1 with an average #PHBA/COOH ratio of 5.0. As expected, solution viscosities of ungrafted copolymers increase moderately as Tg increases. However, viscosity of GB1, an anisotropic dispersion throughout most of the concentration range studied, was substantially lower than that of the copolymer from which it was made. The viscosity range 0.1 to 0.2 Pa.s (a viscosity suitable for spray application of coatings) was attained at about 40 to 45 wt. % with the ungrafted polymers and at about 45 to 50 wt. % with L-C copolymer GB1.

The effect of #PHBA/COOH ratio on viscosity was studied. B2 is an ungrafted acrylic copolymer with $\overline{M}_n$ of about 15,000, Tg of $0°$ C., and functionality of 5 mol %. GB2a and GB2b are L-C graft copolymers prepared from B2 with actual #PHBA/COOH ratios of 4.8 and 3.2, respectively. Again, viscosities of anisotropic dispersions of the grafted copolymers were significantly lower than solutions of the copolymers from which they were made. It appears that increasing #PHBA/COOH ratio slightly reduces viscosity of the dispersions. Viscosity of dispersions of a third L-C copolymer in this series, GB2c (#PHBA/COOH ratio=4.1) was intermediate between GB2a and GB2b.

The behavior of L-C copolymer/MIBK mixtures depended on temperature, concentration and #PHBA/COOH ratio. Behavior of two copolymers, GB2b (#PHBA/COOH=3.2) and GB2a (#PHBA/COOH=4.8) are from the same acrylic copolymer substrate; they differ only in #PHBA/COOH ratio. Both copolymers formed transparent isotropic "solutions" (A) at low concentrations and/or at elevated temperatures. At lower temperatures both copolymers formed biphasic states (B) and anisotropic states (C) at high concentrations. This sort of behavior is typical of lyotropic L-C polymers. Increasing #PHBA/COOH ratio from 3 to 5 decreases solubility, shifting the phase diagram by about 10 wt % as shown.

PHBA/COOH ratio strongly affected the concentrations at phase boundries. As #PHBA/COOH ratio increases the phase boundaries shift to lower concentrations. Temperature also affect the phase boundaries. For example, both the biphasic state and the anisotropic state become isotropic (i.e., they "clear") when heated. The clearing temperatures increased as the #PHBA/COOH ratios increased.

Properties of cast films of selected L-C acrylic copolymers were compared with those of a series of ungrafted, amorphous acrylic copolymers (A1–A10). Three empirical indicators of film properties were used: crosshatch adhesion, reverse impact resistance and pencil hardness. Adhesion was good in every case; other results are shown in Table 15.

Film properties of the amorphous copolymers were poor. When calculated Tg was below 25 C, the films were very soft, and when it was higher they were very brittle. When $\overline{M}_n$ was below 30,000 impact resistance was negligible regardless of Tg. Copolymer A10 ($\overline{M}_n$=39,500 and Tg=$+10°$ C.) had the best properties in the series, although films are too soft for practical use.

Film properties of representative L-C copolymers were substantially better than those of amorphous counterparts (Table 15). Reverse impact resistance of 65 to 80 in-lb is attainable with backbone Mn as low as 15,000, and pencil hardness of H to 3H is attainable with Tg as low as $-10°$ C.

TABLE 15

Comparisons of film properties between amorphous and LC acrylic copolymers:

| # | $\overline{M}_n$ (backbone) (calcd) | Tg (C) | # PHBA/ COOH | Rev. Imp. (in-lb) | Hardness |
|---|---|---|---|---|---|
| Amorphous acrylic copolymers | | | | | |
| A1 | 5,600 | 30 | 0 | 10 | H-2H |
| A2 | 5,200 | 15 | 0 | 10 | 2B |
| A3 | 11,000 | 30 | 0 | 10 | H-2H |
| A4 | 15,600 | 30 | 0 | 10 | H-2H |
| A5 | 14,800 | 15 | 0 | 10 | B |
| A6 | 15,100 | 0 | 0 | (sticky) | |
| A7 | 28,300 | 20 | 0 | 10 | 2H |
| A8 | 29,100 | 10 | 0 | 25 | B |
| A9 | 28,900 | 0 | 0 | (slight sticky) | |
| A10 | 39,500 | 10 | 0 | 40 | HB |
| LC acrylic copolymers | | | | | |
| GB1 | 14,500 | $-10$ | 5.2 | 80 | H |
| GB2a | 15,130 | 0 | 5.0 | 65 | 2H |
| GA11 | 15,700 | $-10$ | 4.8 | 70 | H |
| GA12 | 28,450 | $-10$ | 5.1 | 80 | 3H |

Note:
functionality of all the above polymers is 5% by mol.

It is evident from the above results that films made from L-C acrylic copolymers can have substantially better hardness and impact resistance than those made from comparable amorphous copolymers.

Preliminary Guidelines for LC Copolymer Design Having—established that liquid crystallinity can dramatically improve film properties, a second objective was addressed to develop preliminary guidelines for copolymer design to optimize film properties of non-cross-linked acrylic coatings. Variables studied included $\overline{M}_n$, Tg, functionality (number of graft segments), flexible spacer effects, and #PHBA/COOH ratio (length of graft segments). Results are shown in Tables 16 through 20.

Effects of $\overline{M}_n$ of ungrafted and grafted acrylic copolymer backbones are shown in Table 16. Tg, $T_{cl}$, and adhesion were essentially independent of $\overline{M}_n$ regardless of the presence or absence of flexible spacer. However, reverse impact resistance and hardness increased greatly with $\overline{M}_n$. L-C copolymers with backbone $\overline{M}_n$ of 15,000 and 28,000 had excellent reverse impact resistance ($>70$ in-lb) and good hardness (H - 2H) when Tg, functionality, and #PHBA/COOH ratio were optimal.

TABLE 16

Effects of acrylic backbone Mn on the film properties of LC copolymers:

| # | Backbone $\overline{M}n$ | # PHBA/ COOH | $T_g$ (C) (measured) | $T_{cl}$ | Rev. Imp. (in-lb) | Hardness | Crosshatch adhesion |
|---|---|---|---|---|---|---|---|
| (a). Copolymers with flexible spacer: | | | | | | | |
| GB3 | 5,050 | 5.1 | 4 | 175 | 35 | 2B | 100% |
| B3 | 5,050 | 0 | 0 | — | 10 | (sticky) | 100% |
| GB4 | 10,800 | 4.9 | 5 | 174 | 60 | H | 100% |
| B4 | 10,800 | 0 | 1 | — | 10 | (sticky) | |
| GB2a | 15,130 | 4.8 | 4 | 174 | 70 | 2H | 100% |
| B2 | 15,130 | 0 | 0 | — | 10 | (sticky) | 100% |
| GB5 | 28,200 | 5.2 | 5 | 174 | 80 | 2H | 100% |
| B5 | 28,200 | 0 | 2 | — | 20 | 2B | 100% |
| (b). Copolymers without flexible spacer: | | | | | | | |
| GA13 | 4,870 | 5.2 | −2 | 175 | | (too sticky) | 100% |
| A13 | 4,870 | 0 | −9 | — | | (too sticky) | 100% |
| GA14 | 9,945 | 5.0 | −3 | 174 | 45 | HB-H | 100% |
| A14 | 9,945 | 0 | −10 | — | 10 | (sticky) | |
| GA15 | 14,865 | 4.9 | −2 | 173 | 70 | H | 100% |
| A15 | 14,865 | 0 | −9 | — | 10 | (sticky) | 100% |
| GA16 | 28,500 | 5.1 | −4 | 174 | 80 | H | 100% |
| A16 | 28,500 | 0 | −8 | — | 30 | (sticky) | 100% |

Note:
The functionality of all the acrylic polymers is 5% by mol.

Tg effects for graft copolymers having a functionality of 5 mol % are shown in Table 17. It can be seen that grafting oligo-PHBA has only a slight effect on Tg of the amorphous backbone of the copolymer, increasing it by about 4° to 5° C. Backbone Tg has only a modest effect on clearing temperatures ($T_{cl}$) of the mesophases; about 5,000, similar trends were observed for higher $\overline{M}_n$s. It can be seen that increasing functionality increased Tg and $T_{cl}$. Increasing functionality increased hardness but had an adverse effect on reverse impact resistance. In general, films with functionality above 7.5 mol % had poor reverse impact resistance.

TABLE 18

Effects of functionality on the film properties of the LC acrylic copolymers:

| # | Functionality (mol %) | # PHBA/ COOH | wt % PHBA in polymer | Tg (C) (measured) | $T_{cl}$ | Imp. (in-lb) | Rev. Hardness | Crosshatch Adhesion |
|---|---|---|---|---|---|---|---|---|
| GA17 | 5 | 4.9 | 19.9 | 7 | 173 | 35 | 3B | 100% |
| GA18 | 7.5 | 5.2 | 25.6 | 9 | 174 | 20 | HB | 100% |
| GA19 | 10 | 4.8 | 32.1 | 14 | 181 | 10 | H-2H | 100% |

Notes:
Mn of acrylic backbones is 4,800 ± 300 and calcd Tg is 0C.

$T_{cl}$ increased by 6° C. as backbone Tgs increased from −10° to +10° C. However, backbone Tg substantially affected the empirical film properties. Reverse impact resistance ranged from poor (<10 in-lb) when backbone Tg was 10° C. to excellent (>80 in-lb) when Tg was −10° C. Hardness increased with backbone Tg.

The effects of the presence of flexible spacer between the acrylic backbone and the oligo-PHBA segments are exemplified in Table 19. The flexible spacer reduces the effect of grafting on Tg. Impact resistance improved when flexible spacer was present. However, the effect of flexible spacer on reverse impact resistance appeared

TABLE 17

Effects of the acrylic backbone Tg on the film properties of the LC acrylics:

| | Tg (C) | | | | | | |
|---|---|---|---|---|---|---|---|
| # | Backbone (calcd) | After Grafting (Measured) | # PHBA/ COOH | $T_{cl}$ (C) | Rev. Imp. (in-lb) | Hardness | Crosshatch Adhesion |
| GB1 | −10 | −5 | 5.2 | 171 | 80 | H-2H | 100% |
| GB2a | 0 | 4 | 5.0 | 173 | 65 | 2H | 100% |
| GB6 | 10 | 14 | 4.9 | 177 | 10 | 2H-3H | 100% |

In Table 18, L-C copolymers having different functionalities are compared. While the reported data were obtained for L-C copolymers with backbone $\overline{M}_n$s of less substantial when the backbone Tg was decreased to about −10° C. Films with flexible spacer were slightly softer than those without one.

TABLE 19

Effects of flexible spacer on the film properties of the LC acrylic copolymers:

| # | Tg (C) Backbone (calcd) | Tg (C) After Grafting (measured) | $T_{cl}$ (C) | #PHBA/COOH | Rev. Imp. (in-lb) | Hardness |
|---|---|---|---|---|---|---|
| GB2a | 0 | 4 | 173 | 4.8 | 70 | 2H |
| GA20 | 0 | 7 | 175 | 4.9 | 10 | 2H-3H |
| GB1 | −10 | −5 | 171 | 5.0 | 80 | H |
| GA11 | −10 | −2 | 173 | 4.9 | 70 | H-2H |

Effects of #PHBA/COOH ratio are exemplified in Table 20. As this ratio increased, Tg (after grafting) increased slightly, $T_{cl}$ of L-C phase increased significantly, reverse impact resistance increased greatly, and hardness increased slightly.

TABLE 20

Effects of average # PHBA/COOH on the film properties of LC acrylics:

| # | # PHBA/COOH | Tg (C) | $T_{cl}$ | Rev. Imp. (in-lb) | Hardness | Crosshatch adhesion | Appearance |
|---|---|---|---|---|---|---|---|
| GB2b | 3.2 | 3 | 159 | 30 | B-HB | 100% | TL |
| GB2c | 4.1 | 3 | 164 | 45 | H | 100% | OP |
| GB2a | 4.8 | 4 | 174 | 70 | 2H | 100% | OP |

Notes
1. TL = translucent; OP = opaque.
2. Acrylic backbone: $M_n$ = 15130, calcd Tg = 0 C, and functionality = 5% by mol.

Appearance of films were also greatly influenced by the PHBA/COOH ratio. At functionality of 5 mol %, films were translucent when this ratio was about 3, but they were opaque when it was 4 or above.

To summarize the observations in this example, it appears that the following guidelines may be useful in designing L-C acrylic copolymers for coatings binders:

(1) Tg of the amorphous part of the copolymer may be low; the optimum for a given end use may be in the range of −20° to 0° C. Amorphous copolymers of such low Tg are normally far too soft to be usable as coatings. Acrylic lacquers are usually formulated with Tg near or slightly above the highest service temperature. Apparently the presence of L-C domains can harden low Tg films, yet the elasticity associated with low Tg is at least partly retained.

(2) The best combination of hardness and elasticity is attained when functionality is low but PHBA/COOH ratio is high.

(3) Flexible spacer improves impact resistance when backbone Tg is 0° C. or higher but has relatively little effect when Tg is −10° C. Introduction of flexible spacer by the method used in this study has the disadvantage of placing relatively unhindered ester groups between the acrylic backbone and the mesogenic group; these ester groups are relatively vulnerable to hydrolysis in water and weather. Other potential routes for introducing flexible spacers are costly. Thus for practical purposes it may be preferable to use low Tg backbones and dispense with flexible spacer.

EXAMPLE 4

In this example it will be demonstrated that the L-C acrylic copolymers of Example 3 can be cross-linked with a melamine resin to provide hard, tough enamels.

Amorphous acrylic copolymers composed of MMA, BA, and acrylic acid having calculated Tg of −30°, −10°, and +10° C. and $\overline{M}_n$ of 4,700±200 and functionality of 5 mol percent acrylic acid were synthesized as described in Example 2. Each was grafted with PHBA, as described, to provide L-C graft copolymers having PHBA-COOH ratios of 4±0.2. Liquid crystallinity was confirmed by polarizing miscroscopy.

Each of the above copolymers was dissolved or dispersed in a methyl isobutyl ketone solution containing HMMM crosslinking resin and p-toluene sulfonic acid (p-TSA) catalyst. The weight ratio was 70.6/28.6/0.7 L-C copolymer/HMMM/p-TSA. The mixture was exposed to ultrasonic energy to promote mixing. It was cast on untreated cold, rolled steel panels and baked in a forced air oven for 30 minutes at 150° C to give a cured film.

Knoop hardness and reverse impact resistance of the 6 enamels were tested as described in Example 2. Results are shown in Table 21.

TABLE 21

| Copolymer Tg and Type | Knoop Hardness | Reverse Impact Resistance |
|---|---|---|
| −30, Amorphous | 15 | 80 |
| −10, Amorphous | 17 | 60 |
| +10, Amorphous | 19 | 40 |
| −30, L-C | 27 | 80 |
| −10, L-C | 34 | 80 |
| +10, L-C | 45 | 5 |

Thus, it is evident that the presence of mesogenic groups improved both hardness and impact resistance for enamels made from copolymers having Tgs of −30° and −10° C. When Tg is +10, the impact resistance of the L-C film is inferior but the finish is extraordinarily hard. For comparison, the hardness of current auto topcoat enamels is about about 12 Kn.

In other experiments it was determined that the optimum $\overline{M}_n$ for HMMM crosslinked L-C copolymers for high-solids enamels is about 5,000. As shown in Example 2, higher molecular weights are desirable for uncrosslinked enamels.

EXAMPLE 5

L-C telechelic oligoester diols are prepared and cross-linked with a resin, preferably a melamine resin, to provide the coatings of this example. After baking, the coatings retained their L-C character which provided the improved characteristics to the coatings. The properties of the coatings were tested on cold-rolled steel panels.

The ratio of L-C telechelic oligoester diols to resin should be in the range of 95:5 to 50:50, and is preferably about 70:30. The L-C oligoester diols were prepared by reacting 4,4'-terephthaloyldioxydibenzoyl (TOBC) with molar equivalents of aliphatic diols. Non-liquid crystal diols (2a-g) were prepared for comparison, the L-C and non-L-C diols having the general formula:

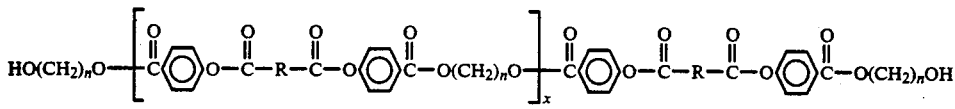

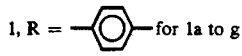

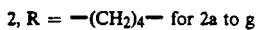

| | 1a | 1b | 1c | 1d | 1e | 1f | 1g |
|---|---|---|---|---|---|---|---|
| | 2a | 2b | 2c | 2d | 2e | 2f | 2g |
| n = | 4 | 5 | 6 | 7 | 8 | 10 | 12 |

The value of n, sometimes referred to as spacer length, should preferably be in the range of 5 to 12. When $n=5$ or less, there is poor miscibility in forming enamels and at higher n values mixing becomes increasingly difficult.

Coatings were prepared by mixing the L-C oligoester diols or polyols after solubilization with melamine or polyisocyante resin in the presence of an accelerator. The coatings were cast on panels and baked at cross-linking temperatures for testing. L-C oligoester polyols may be prepared by replacing part of the aliphatic diol with a triol or tetrol.

Testing

Proton NMR spectra were recorded at 34° C. on a Varian Associates EM-390 90 MHz NMR spectrometer, using Me$_4$Si as internal standard. IR spectra were recorded at 25° C. on a Mattson Cygnus FT-IR using films cast on NaCl plates with polystyrene as standard. A DuPont model 990 thermal analyzer was used for differential scanning calorimetry (DSC) at heating rates of 10/min. After the crystalline-mesophase transition temperature ($T_m$) was reached, the temperature was held for 1 min. before the scan was resumed. Capillary melting points were used to confirm the thermal data. $\overline{M}_n$ and $\overline{M}_w$ were determined by gel-permeation chromatography (GPC) with a Waters model 520 pump equipped with a model R401 refractive index detector, a model M730 data analyzer, and Ultrastragel 100 A, 500 A, 1000 A, and 10000 A columns. Mass analysis was performed. A Leitz Labolux microscope equipped with a polarizing filter was used for optical micrographs at 500x magnification; diols were observed immediately after heating to $T_m$, enamels were observed at room temperature.

Seven samples of the L-C oligoester diols were prepared and designated 1a to 1g, inclusive and, for comparison, seven samples of non L-C oligoester diols were prepared and designated 2a to 2g, inclusive, having corresponding n values and made into amorphous coatings. These corresponding n values are indicated, as above.

In the preparation of the products, reagent materials were used and the steel panels which were coated were commercially available cold-rolled steel panels sold under the trademark Bonderite 1000 and having a size of 3 inches by 9 inches by 24 GA.

Preparation of 1a-g

TOBC was prepared from terephthaloyl chloride and p-hydroxybenzoic acid (PHBA) as described by Bilibin et al at *Polymer Science USSR* (1984) 26. 2882. TOBC (0.005 mol), diol (0.025 mol), and diphenyl oxide (10 mL) were placed in a 100 mL single-necked round-bottomed flask equipped with a magnetic stirring bar, a distillation adapter, and a septum. The flask was flushed with argon for 15 min., and was stirred and heated in an oil bath at 190°-200° C. under slow argon flow. The reaction mixture became homogeneous after 5 minutes and the evolution of HCl was observed. The reaction was continued until the evolution of HCl was no longer detectable by moistened litmus paper (405 hr.). The hot reaction mixture was poured cautiously into 100 mL of toluene and cooled. The oily residue that separated was dissolved in CH$_2$Cl$_2$, washed 3 times with water, and dried over anhydrous MgSO$_4$. The solution was filtered and concentrated using a rotary evaporator. The residue was precipitated from methanol. Yields were 87-92% based on TOBC $^1$H NMR for 1c in CDCl$_3$; 1.4 (broad), 3.6 (triplet), 4.2 (multiplet), 6.8 (doublet), 8.1 ppm (multiplet). FT-IR for 1c: 3420, 2960, 2938, 1720,1606, 1512 cm$^{-1}$. L-C diols 1a-g had similar spectra.

For comparison to the L-C oligoester diols of this example, non-L-C oligoester diols were prepared from diols in which R=(CH$_2$)$_4$ and made into amorphous coatings.

Preparation of 2a-g

The diacid chloride precursor was prepared by substituting adipoyl chloride for terephthaloyl chloride in Bilibin's procedure. Reaction of this precursor with diols was carried out as described for 1a-g except that the products were not poured into toluene. Diols 2a-g were resinous solids which solidified on standing.

Enamel formation

Oligoester diols 1b-g and 2a-g, HMMM [hexakis (methyloxy-methyl) melamine resin], methyl isobutyl ketone (MIBK), as a solvent and p-toluenesulfonic acid (p-TSA) as a catalyst were thoroughly mixed in a 70/30/30/0.3 wt. ratio. The solution was cast on cold rolled steel panels and baked at 150C for 30 minutes. Less soluble L-C diols 1e-g were melted, dispersed in solvent, mixed with HMMM and immediately cast as films. miscibility. The properties of the cross-linked enamels are summarized in Table 23.

TABLE 23

Properties of Enamels Prepared from 1b–g and 2a–g. Diol: HMMM:p-TSA 70:30:0.3 by wt., cure cycle 150/30 min.

| | mesogenic samples | | | | | | controls |
|---|---|---|---|---|---|---|---|
| | 1b | 1c | 1d | 1e | 1f | 1g | 2a–g |
| spacer length (n) | 5 | 6 | 7 | 8 | 10 | 12 | 4–12 |
| reverse impact (in-lb) | 80 | 50 | 80 | 50 | 50 | 55 | 8–15 |
| direct impact (in-lb) | 80 | 50 | 80 | 50 | 50 | 50 | 10–15 |
| pencil hardness (ASTM-D 3363) | 6H | 6H | 5H | 6H | 5H-6H | 6H | H-2H |
| adhesion[a] (ASTM-D 3363) | 5B | 5B | 5B | 5B | 5B | 5B | 5B |
| acetone rubs (double rubs) | 200 | 200 | 200 | 200 | 200 | 200 | 200 |
| flexibility (ASTM-D 522) | 100% | 100% | 100% | 100% | 100% | 100% | 100% |
| dry film thick.[b] | 0.5 | 0.5 | 0.5 | 0.5 | 0.5 | 0.5 | 0.5 |
| $T_g$[c] | 17 | 35 | 23 | 16 | 15 | 22 | 17–28 |
| appearance | transparent, glossy | | | | | | |

[a] 5B is 100% cross-hatch adhesion;
[b] units are 1/1000 in.;
[c] onset of transition, determined by DSC.

Oligoester Diols. The physical properties of 1a–g obtained by GPC, DSC and polarizing optical microscopy are summarized in Table 22.

TABLE 22

Physical Properties of 1a–g

| diol | n | $M_{Th}$[a] | $M_n$ | $M_w$ | PDI | $T_m$ | $T_i$ | texture |
|---|---|---|---|---|---|---|---|---|
| 1a | 4 | 550 | 480 | 720 | 1.5 | 110 | 204 | — |
| 1b | 5 | 578 | 530 | 740 | 1.4 | 58 | 207 | smectic |
| 1c | 6 | 606 | 570 | 810 | 1.4 | 75 | 349 | smectic |
| 1d | 7 | 634 | 610 | 850 | 1.4 | 47 | 300 | smectic |
| 1e | 8 | 662 | 650 | 910 | 1.4 | 82 | 302 | smectic |
| 1f | 10 | 718 | 680 | 950 | 1.4 | 80 | 231 | nematic |
| 1g | 12 | 774 | 720 | 1130 | 1.4 | 90 | 220 | smectic |

[a] theoretical molecular weight for x = 0

$^1$H NMR and IR spectra were consistent with structures 1a–g and 2a–g assuming that partial chain extension occurred as indicated by GPC. Low $\overline{M}_n$ values and slightly high H analyses suggest that small amounts of unreacted HO(CH$_2$)$_n$OH were present in the products.

The L-C nature of 1a–g was demonstrated by DSC in which two first order transitions were observed; the crystalline-mesophase transition temperature ($T_m$), and the mesophase-isotropic transition temperature ($T_i$). The thermal data revealed an odd-even spacer effect for $T_m$. Smectic-nematic transitions were not evident in the DSC.

In contrast, diols 2a–g were apparently not L-C materials. Only one first order transition was observed by DSC.

The mesophases of 1a–g were observed in polarized optical micrographs taken immediately after melting the sample. Textures were identified by comparing appearance with published micrographs. See: Noel, *Polymeric Liquid Crystals*, Plenum Press, New York, (1984). A nematic texture is observed for 1f, while more highly ordered smectic textures are observed for 1b–e and 1g. Crystals were observed by microscopy for diols 2a–g Cross-linked Enamels. Diols 1a–g and 2a–g were cross-linked with HMMM at 150° C., which the temperature range at which 1 are liquid crystalline. Enamel formation o 1a was nearly impossible because of its poor As shown in Table 23, all enamels had excellent adhesion, solvent resistance, and flexibility. The L-C enamels were far superior to control enamels in both hardness (5H-6H vs. H-2H) and impact resistance (50 to 80 in-lb vs. 8 to 15 in-lb). The odd spacers 1b and 1d afforded the best properties. Spacer variations did not measurably affect enamel properties in the control oligoesters.

DSC thermograms of the cross-linked enamels revealed onset of glass transitions (Tg) ranging from Tg 15° to 35° C. for L-C enamels 1b–g and amorphous enamels 2a–g. An odd-even pattern was not observed in either type.

Polarized optical micrographs revealed L-C regions in the cross-linked enamels of 1b–g. Enamels of 2a–g appeared amorphous. IR spectra of the baked L-C and amorphous enamels had peaks attributable to unreacted OH groups at 3420 cm$^{-1}$ (OH stretch) and at 1271 cm$^{-1}$ (OH bend).

In summary, the method used to make oligoester diols 1a–g was adapted from Bilibin's method for making chain L-C high polymers by using a five-fold excess of HO(CH$_2$)$_n$OH. Spectral, chromatographic and mass analytical evidence all indicated that the expected products were obtained from the adapted process.

GPC and analytical data suggested that the structures with x=1 and x=2 predominate; smaller amounts of structures with x >2 and of HO(CH$_2$)$_n$OH are probably present in 1a–g and 2a–g.

The thermal behavior of 1a–g observed by DSC confirms the presence of mesophases and is typical of low molecular weight liquid crystals. The odd-even effect is of interest because of its direct affect on the physical properties of the L-C diols. The lower $T_m$ for 1b and 1d is consistent with the higher entropy of activation for crystallization of odd-n spacers, demonstrated in several main chain L-C polymers, Ober et al, *Advances in Polymer Science, Liquid Crystal Polymers I*, Springer-Verlag (1984), Vol. 59. The apparent absence of nematic-smetic transitions in the DSC suggests the observed morphology exists for the entire mesophase.

The nematic texture of oligomeric L-C diol 1f is the same as reported for the homologous main chain L-C high polymer, Lenz, *Journal Polymer Science*, Polymer Symposium (1985) 72, 1–8.

Oligomeric diols 1b–d were soluble in MIBK and were miscible with the HMMM cross-linker; films were readily cast. Higher melting diols 1e–g were less miscible, but the consistently good film properties indicate that adequate mixing was achieved. Mixing of diol 1a with HMMM was inadequate to produce uniform films.

Enamels made from odd-n L-C diols 1b and 1d had better impact resistance than those made from even-n diols. This effect may be attributed to an odd-even effect, although other variables may be involved.

The enhanced properties of the L-C diol enamels are not simply explainable by the monomer raising the Tg of the coating. In fact, Tgs of the cross-linked enamels of 1b–g are abnormally low for hard coatings, and are similar to the much softer control enamels.

A non-L-C linear oligoester diol is prepared by heating a mixture of phthalic acid (PA), adipic acid (AA) and neopentyl glycol (NPG). The reaction of the mixture is effected under $N_2$ at 230C with removal of $H_2O$ until the acid number was less than 10 mg KOH/g. The sum of the mols of acids should be less than the mols of diols and the ratio should be in the range of 1:2 to 1:1.1. A particular example of a mixture of PA, AA and NPG at a mol ratio of 1:1:3 was highly satisfactory.

A mixture of the diol or polyol, PHBA, an acid catalyst and particularly p-TSA and solvent was heated under $N_2$ in a 3-neck flask equipped with stirrer, Dean-Stark trap, condenser and thermometer. The PHBA was in substantially pure form so as not to affect catalytic action. The PHBA/diol or PHBA/polyol weight ratio varied from 20/80 to 60/40, but the preferred ratio is about 40/60; 0.2 weight % of p-TSA was used as an acid catalyst to provide a predominantly phenolic L-C oligoester diol or polyol. About 10 weight % of solvent was used; the amount was adjusted to maintain the temperature in the range of 210° C. to 250° C., and preferably in the range of 227° to 233° C. In an actual preparation the temperature was held at 230 +/−3C. Distillate (cloudy $H_2O$) was collected in the Dean-Stark trap during 9 to 11 hr. The reaction mass was cooled to 115° C., and MIBK was added to yield a solution (20/80 PHBA/diol ratio) or suspension (other PHBA/diol ratios) of the crude L-C polyol. A preferred solvent is "Aromatic 150" sold by Exxon.

It is important that the acid catalyst be used and that the temperature be controlled to provide the L-C predominately phenolic oligoesters of the invention. Likewise, it is important that the PHBA be used in the weight ratio range specified to give the L-C diols desired.

The linear oligoester diol was heated with salycilic acid and with MHBA using a similar procedure to yield modified polyols. 60% to 80% of theoretical distillation was obtained.

Purification

The crude L-C polyols made from 20/80 and 30/70 PHBA/diol ratios were concentrated and dissolved in $CH_2Cl_2$. The solution was washed 5 times with $H_2O$, dried with $Na_2SO_4$, and concentrated on a rotary evaporator. The residues were heated at 120° C. to constant weight. The crude L-C polyols made from 40/60 to 60/40 ratios were purified similarly but were not washed with water. They were heated at about 80° C. under vacuum on a rotary evaporator to remove small amounts of volatile, crystalline material.

Enamel Preparation

Solutions or mixtures of L-C polyol, HMMM and p-TSA in a 75/25/0.25 weight ratio were cast on cold-rolled panels and baked at 175° C. for the specified time. Dry film thicknesses were 20 to 25 um.

Characterization and testing

IR spectra were recorded using a Perkin-Elmer 137 NaCl-prism spectrophotometer. A DuPont model 990 thermal analyzer was used for differential scanning calorimetry (DSC) at heating rates of 10/min. After the crystalline-mesophase transition temperature ($T_m$) was reached, the temperature was held for 1 min. before the scan was resumed. Capillary melting points were used to confirm the thermal data. $\overline{M}_n$ and $\overline{M}_w$ were determined by gel-permeation chromatography (GPC) with a Waters model 520 pump equipped with a model R401 refractive index detector, a model M730 data analyzer, and Ultrastragel 100 A, 500 A, 1000 A and 10000 A columns. Mass analysis was performed. A Leitz Labolux microscope equipped with a polarizing filter was used for optical micrographs at 500x magnification; L-C polyols were cast on glass slides and were dried and observed at 25° C., and enamels were baked at 175° C. for 20 minutes on the glass slides.

Hydroxyl numbers were determined by the pyromellitic dianhydride/imidazole method. See: Demarest, B. O.; Harper, L. E. *Journal of Coating Technology* 1983, 55(701), 65–77. Impact resistance and pencil hardness were tested according to ASTM-D 2793 and ASTM-D 3363, respectively. Solvent resistance was tested by spotting films with methyl ethyl ketone. Potentiometric titration in DMF indicated that a substantial fraction of phenolic groups are present in the oligomers, but it has not yet been feasible to reproducibly obtain quantitative results because precipitate formed during titration.

This preparation yields PHBA-modified oligomers, apparently with side reactions. The odor of phenol was barely detectable in the products, indicating that little phenol had been formed. p-TSA catalyst plays a crucial role. When p-TSA was not used in the 30/70 PHBA/-diol reaction only 75% of theoretical distillate was collected, and the product smelled strongly of phenol. Solvent also plays an important role by helping control temperature and by facilitating removal of water. If desired, the products can be purified as described to remove small amounts of unreacted PHBA and possibly of phenol.

Modification of the PA/AA/NPG diol with salicylic and m-hydroxybenzoic acids apparently did not proceed as smoothly as the modification with PHBA. No liquid crystals could be detected in the products by polarizing microscopy.

Potentiometric titration and infrared spectra (peak at 3400 cm$^{-1}$) indicate that phenolic end groups predominate in the product oligomers.

Molecular weights determined by GPC are provided in Table 26. Also provided are rough estimates of the average number of PHBA units per number average molecule. These estimates were obtained by multiplying product $\overline{M}_n$ by the weight fraction of PHBA charged and dividing the result by 120, the molar mass of PHBA minus water.

TABLE 26
Gel Permeation Chromatography of Polyols

| PHBA/diol wt. | ratio mol | $\overline{M}_n$ | $\overline{M}_w$ | $\overline{M}_w/\overline{M}_n$ | avg PHBA residue/molecule |
|---|---|---|---|---|---|
| 0/100 | — | 1200 | 2000 | 1.7 | — |
| 20/80 | 2.1/1 | 1400 | 2400 | 1.7 | 2.3 |
| 30/70 | 3.6/1 | 1100 | 1900 | 1.7 | 2.8 |
| 40/60 | 5.8/1 | 970 | 1600 | 1.6 | 3.2 |
| 50/50 | 8.8/1 | 870 | 1400 | 1.7 | 3.6 |
| 60/40* | 13/1 | 830 | 1400 | 1.7 | 4.1 |

*Filtered to remove a small fraction of THF-insoluble material.

The L-C character of PHBA-containing oligomers was demonstrated by polarizing microscopy as indicated in DSC data in Table 27 indicate that Tg increases with increasing PHBA/diol ratios except for the 60/40 PHBA/diol ratio.

TABLE 27
Differential Scanning Calorimetry and Polarizing Microscopy of Polyols

| PHBA/diol ratio | 0/100 | 20/80 | 30/70 | 40/60 | 50/50 | 60/40 |
|---|---|---|---|---|---|---|
| Tg (C) | −10 | 7 | 14 | 19 | 27 | 14 |
| Appearance, 500x | clear | a few spots | L-C | L-C | L-C | L-C |

Enamel Coatings Properties

Clear coatings were formed by cross-linking the PHBA-modified oligomers with a standard melamine resin. Baking at 175C was necessary to obtain optimal properties. The cured films were nearly transparent and glossy except for films made from 60/40 PHBA ratio L-C polyol. Adhesion was excellent.

The outstanding feature of enamels made from 40/60 to 50/50 PHBA/diol ratio L-C polyols is that they are both very hard and very impact resistant as shown in Table 28.

TABLE 28
Impact Resistance and Pencil Hardness of Baked Enamels

| PHBA/diol ratio | 0/100 | 20/80 | 30/70 | 40/60 | 50/50 | 60/40 |
|---|---|---|---|---|---|---|
| Baking Time (min) at 175 C. | | | | | | |
| 20 | *(HB) | p(H) | p(H) | p(3H) | p(4H) | f(5H) |
| 40 | *(HB) | p(H) | p(H) | p(3H) | p(4H) | f(5H) |
| 60 | *(HB) | f(H) | p(2H) | p(4H) | f(5H) | f(6H) | p: passes 80 in-lb reverse impact test; f: fails;
*appears to pass but cracks after standing several days.

The enamels described in Table 28 with pencil hardness of 3H to 6H had excellent solvent (methyl ethyl ketone) resistance.

The salycilic acid modified oligomers did not cure at 175° C. The MHBA modified oligomers cured at 175° C. to give hard films, but all failed the 80 in-lb impact resistance test.

Polarizing micrographs showed clear evidence of the presence of birefringent phases in enamel films made from polyols modified by 30 percent or more of PHBA. L-C regions were not visible in cured films made from the PA/AA/NPG polyol or from the MPHA-modified enamels.

The results of the above experiments indicate that mesogenic groups substantially enhance a polymer resin's coating quality. Grafting oligomeric segments derived from PHBA or TPA/PHBA onto coating resins yields resins that contain liquid crystalline (L-C) phases. These phases impart at least three benefits: "solution" viscosity is reduced by the formation of non-aqueous dispersions, dry-to-touch times are sharply reduced, and films are both hardened and toughened. Imparting L-C characteristics to a resin minimizes the hardness/impact resistance tradeoff necessary with non-modified coating resins.

Although the invention has been described with regard to its preferred embodiments, it should be understood that various changes and modifications as would be obvious to one having the ordinary skill in this art may be made without departing from the scope of the invention which is set forth in the claims appended hereto.

The various features of this invention which are believed new are set forth in the following claims.

TABLE 29 a
Monofunctional Derivatives

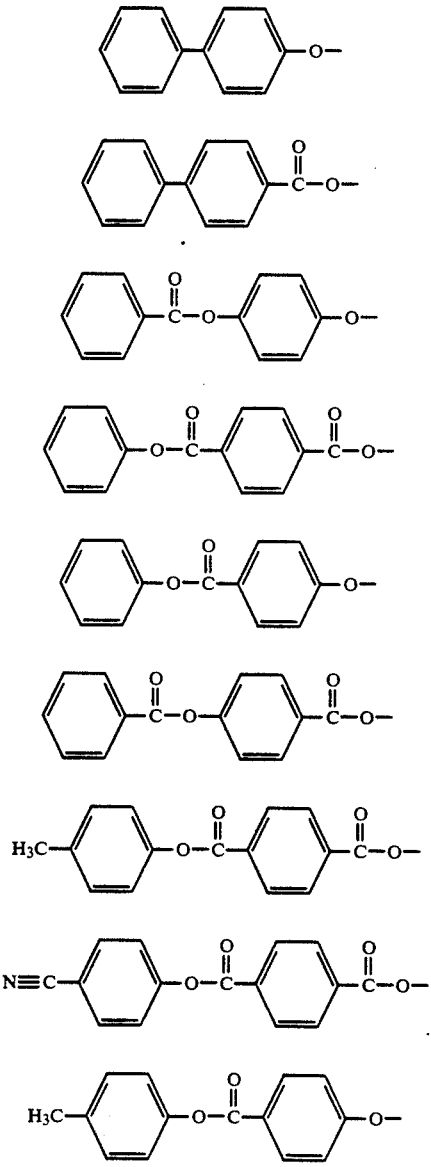

-continued
TABLE 29 a
Monofunctional Derivatives
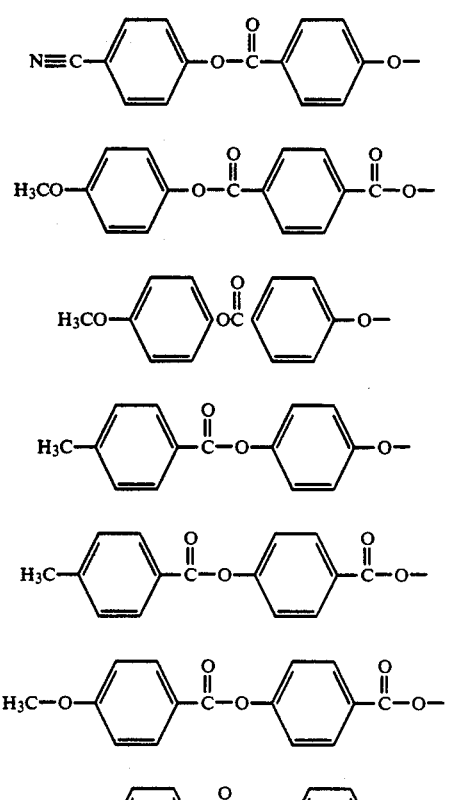
TABLE 29 b
Monofunctional Derivatives
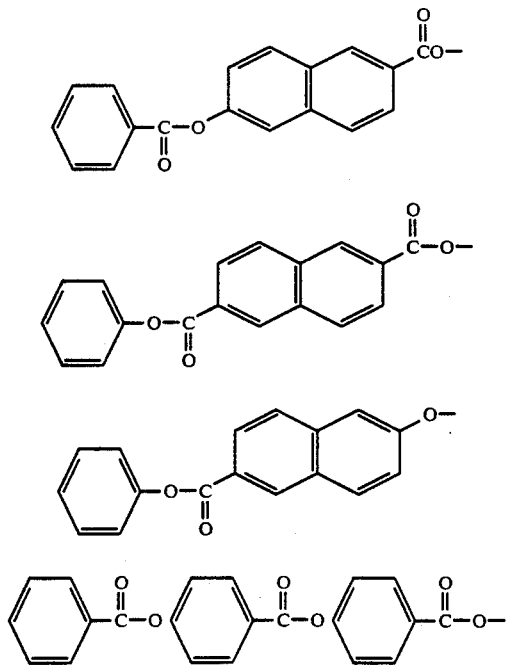
-continued
TABLE 29 b
Monofunctional Derivatives
TABLE 29 c
Monofunctional Derivatives
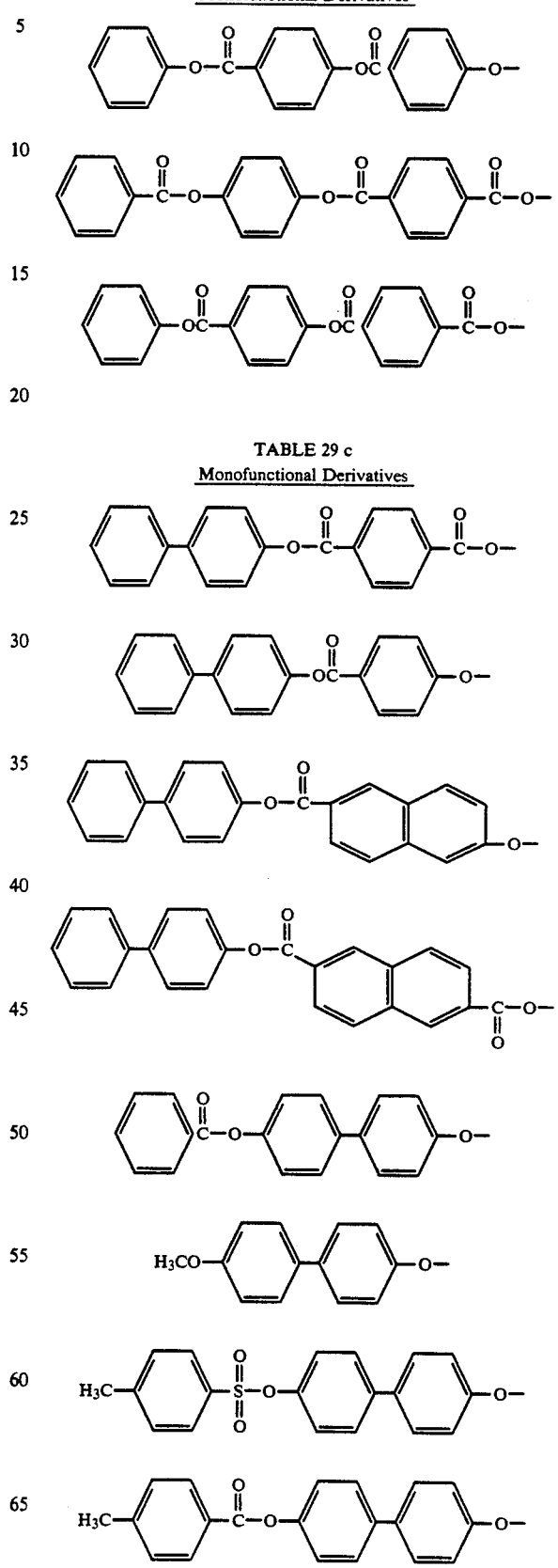

TABLE 29 d
Difunctional Derivatives
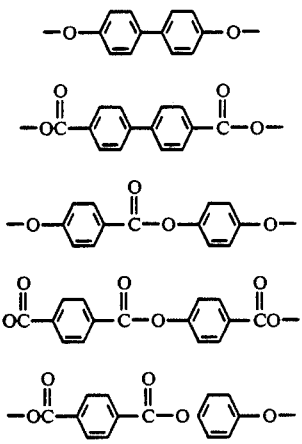
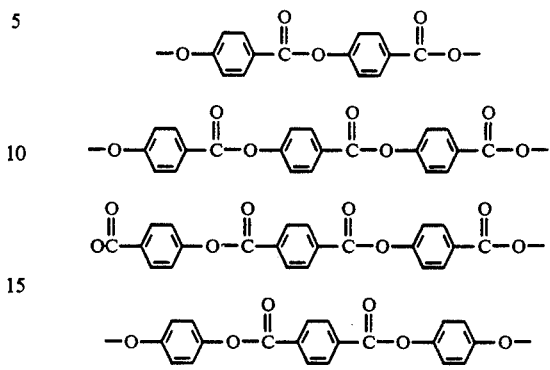
TABLE 29 E
Difunctional Derivatives
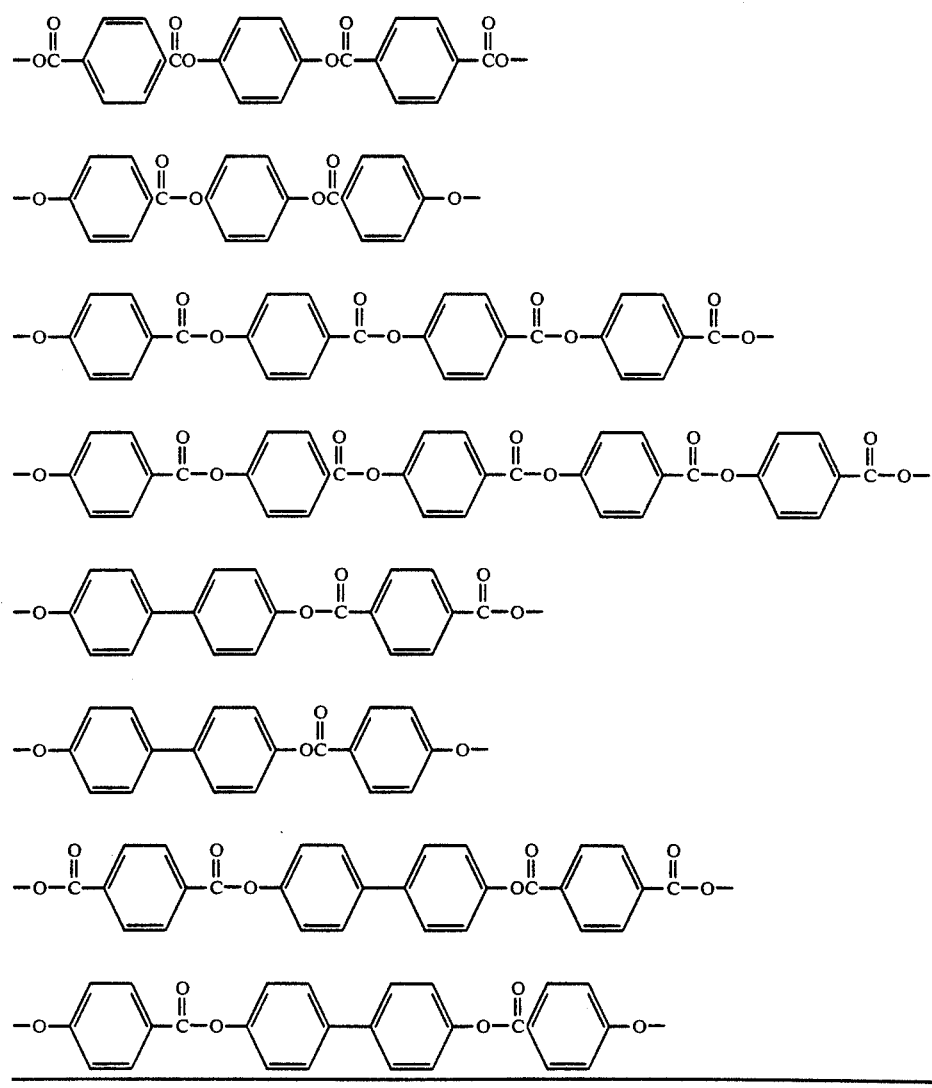

TABLE 29 F
Difunctional Derivatives
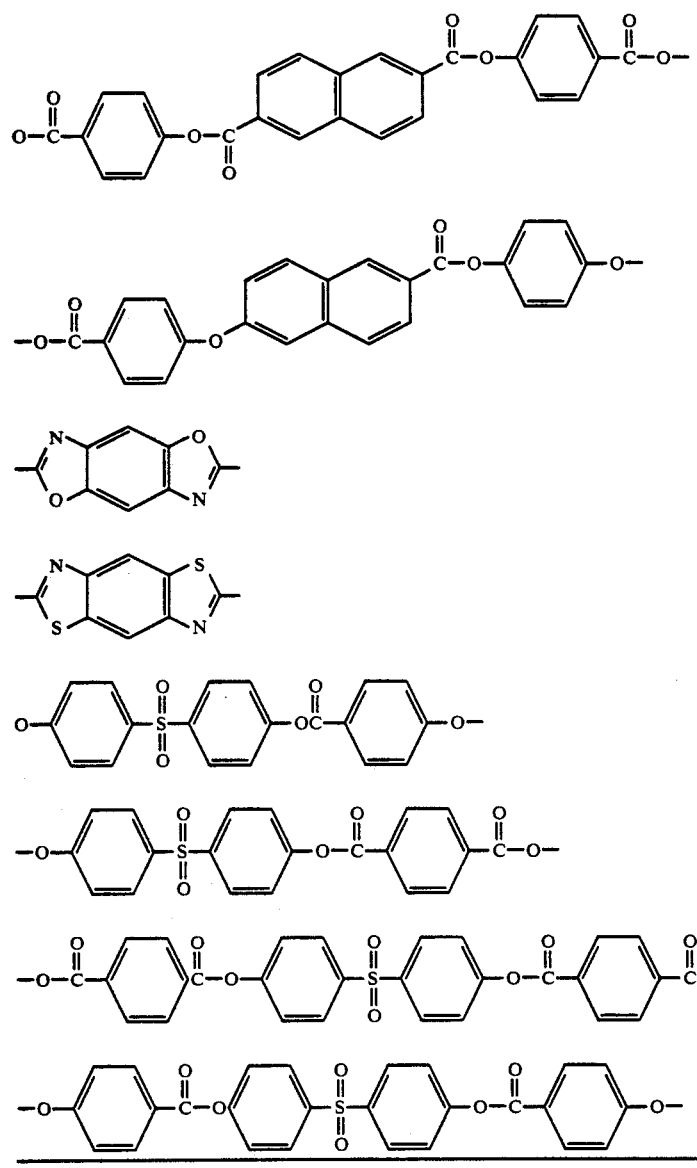
TABLE 29 G
Difunctional Derivatives
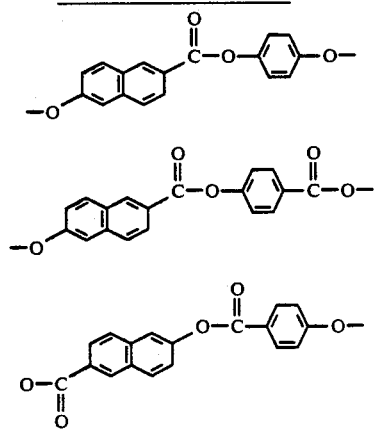
TABLE 29 G-continued
Difunctional Derivatives
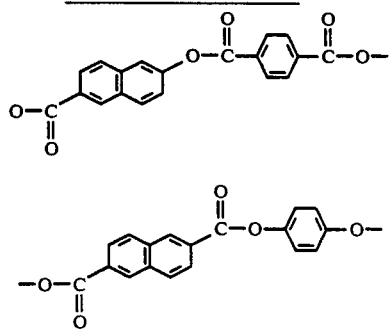

TABLE 29 G-continued
Difunctional Derivatives

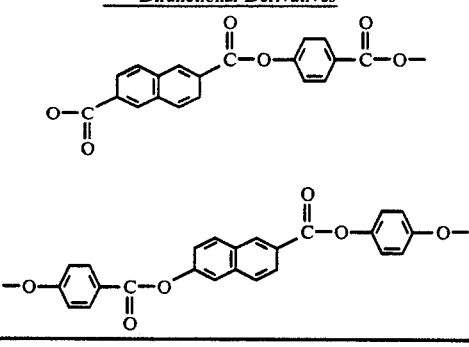

TABLE 29 H
Miscellaneous Derivatives

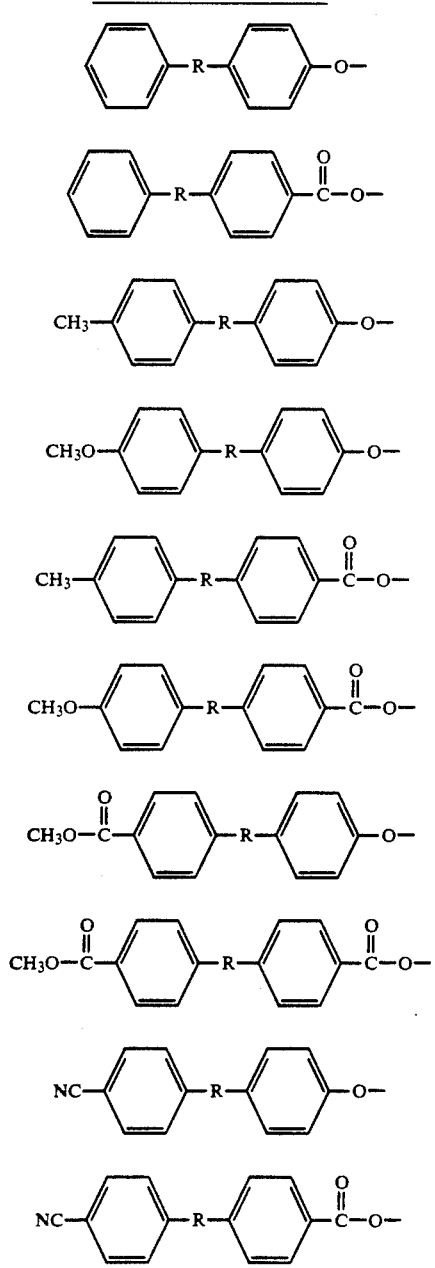

TABLE 29 H-continued
Miscellaneous Derivatives

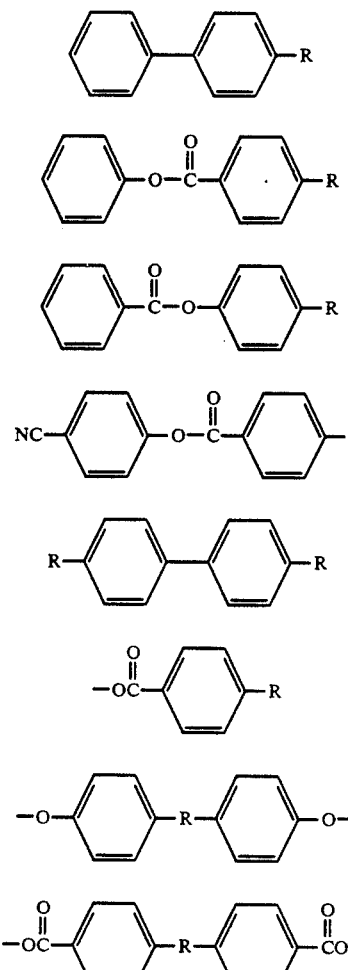

wherein

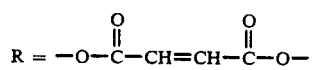

$$R = -O-\overset{O}{\underset{\|}{C}}-CH=CH-\overset{O}{\underset{\|}{C}}-O-$$

What is claimed is:

1. A polymeric vehicle which when applied to a substrate provides a coating binder having a Tg not greater than about 180° C., a pencil hardness of at least about H, and a reverse impact resistance of at least 30 inch-lbs. at a binder thickness of about 1 mil, said polymeric vehicle comprising:
 a cross-linker resin; and
 at least about 35 weight percent, based upon the weight of the polymeric vehicle, of a modified epoxy polymer which is reactive with the cross-linker resin,
 wherein the modified epoxy polymer is an epoxy polymer covalently bound to at least one mesogenic group selected from the group consisting of formulas I, II, III, IV and V such that the modified polymer contains from about 5 to about 50 weight percent mesogenic groups based upon the weight of the modified epoxy polymer wherein the formulas I, II, III, IV and V are I. 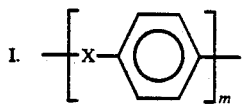

or covalently bonded combinations of such general formula;

II. 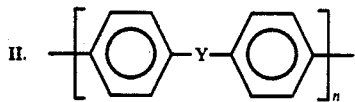

or covalently bonded combinations of such general formula;

III. 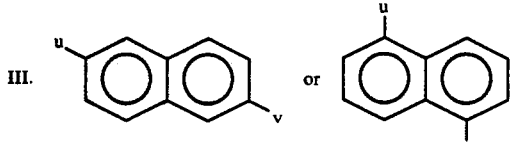 or 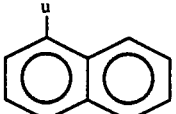

or covalently bonded combinations of such general formulas;

IV. Combinations of I, II, and 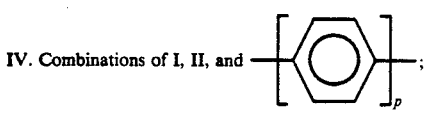;

V. Combinations of III and 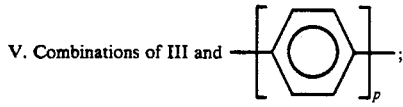;

wherein

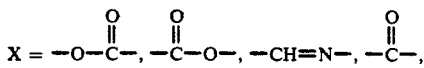

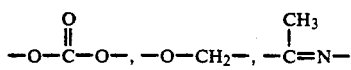

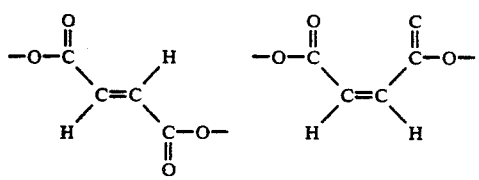

Y = X or 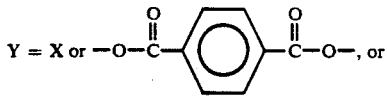

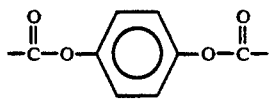

v = 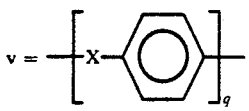

and u = X;
m = an integer from 2 to 8;
n = 1 or 2;
p = an integer from 1 to 4; and
q = an integer from 1 to 3.

2. A polymeric vehicle as recited in 1 wherein the mesogenic group has Formula I.

3. A polymeric vehicle as recited in claim 1 wherein the mesogenic group has Formula II.

4. A polymeric vehicle as recited in claim 1 wherein the mesogenic group has Formula III.

5. A polymeric vehicle as recited in claim 1 wherein the mesogenic group has Formula IV.

6. A polymeric vehicle as recited in claim 1 wherein the mesogenic group has Formula V.

7. A polymeric vehicle as recited in claim 3 wherein

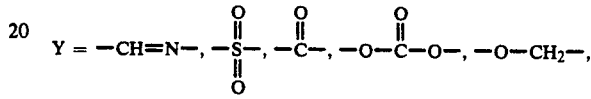

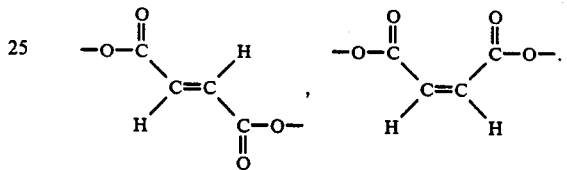

8. A polymeric vehicle as recited in claims 1, 2, 3, 4, 5, 6 or 7 wherein the polymeric vehicle includes a cross-linker resin selected from the group consisting of a polyamine, aminoplast resin and mixtures thereof.

9. A polymeric vehicle as recited in claim 1 wherein the cross-linker resin is a polymer without mesogens.

10. A polymeric vehicle as recited in claims 1, 2, 3, 4, 5 or 6 wherein the polyamine, aminoplast resin, a carboxylic acid, a mercaptan, and a polyisocyanate resin.

11. A polymeric vehicle as recited in claims 1 or 9 wherein the modified epoxy polymer is the reaction product of an epoxy compound and a diol selected from the group consisting of

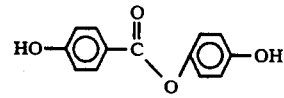

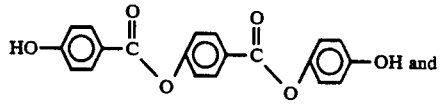 and

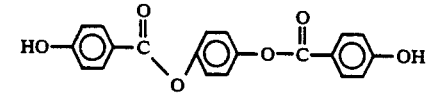

12. A polymeric vehicle as recited in claim 11 wherein the cross-linker resin is selected from the group consisting of a polyamine, aminoplast resin, a carboxylic acid, a mercaptan, and a polyisocyanate resin.

* * * * *